US008417491B2

(12) United States Patent
Trovato et al.

(10) Patent No.: US 8,417,491 B2
(45) Date of Patent: Apr. 9, 2013

(54) 3D TOOL PATH PLANNING, SIMULATION AND CONTROL SYSTEM

(75) Inventors: Karen I. Trovato, Putnam Valley, NY (US); Eric Cohen-Solal, Ossining, NY (US); Douglas Summers-Stay, Edgewater, NJ (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/088,870

(22) PCT Filed: Oct. 6, 2006

(86) PCT No.: PCT/IB2006/053672
§ 371 (c)(1),
(2), (4) Date: Apr. 1, 2008

(87) PCT Pub. No.: WO2007/042986
PCT Pub. Date: Apr. 19, 2007

(65) Prior Publication Data
US 2008/0234700 A1    Sep. 25, 2008

Related U.S. Application Data

(60) Provisional application No. 60/725,185, filed on Oct. 11, 2005.

(51) Int. Cl.
*G06G 7/48* (2006.01)
(52) U.S. Cl. ............................................. 703/6
(58) Field of Classification Search ............. 703/6
See application file for complete search history.

(56) References Cited

U.S. PATENT DOCUMENTS

| 5,870,303 | A | 2/1999 | Trovato et al. |
| 6,604,005 | B1* | 8/2003 | Dorst et al. .................. 700/56 |
| 6,695,774 | B2 | 2/2004 | Hale et al. |
| 6,726,675 | B1 | 4/2004 | Beyar |
| 2004/0249267 | A1 | 12/2004 | Gilboa |

(Continued)

FOREIGN PATENT DOCUMENTS

| EP | 0317020 B1 | 4/1995 |
| JP | 11120327 A | 4/1999 |
| JP | 2005131319 | 5/2005 |
| WO | WO9911189 | 3/1999 |

OTHER PUBLICATIONS

In Re Karen I. Trovato and Leendert Dorst., 42 F.3d 1376 (Fed. Cir. 1994); pp. 1-9.*
Trovato: A* Planning in Discrete Configuration Spaces of Autonomous Systems; PhD Thesis; pp. 1-208; 1996.*

(Continued)

*Primary Examiner* — Hugh Jones

(57) ABSTRACT

A system, apparatus, and method are provided for control of a catheter (including an ablation catheter), bronchoscope/endoscope and beveled needle. Control of a bronchoscope (100) is calculated for a 3D environment based on capabilities of the bronchoscope and the patient morphology. This can be used to plan and simulate an optimal motion, train or compare surgical techniques or automate the procedure. A particular bronchoscope may be recommended based on its form and flexibility as well as based on the personal morphology of the patient rather than relying on statistical norms. For all tools, a 6 dimensional configuration space problem is solved using 3 storage dimensions and a '6D neighborhood' for path planning. The present invention finds the kinematically feasible path from a 'start' to a goal, while avoiding obstacles and dangerous regions.

27 Claims, 15 Drawing Sheets

U.S. PATENT DOCUMENTS

2005/0096589 A1  5/2005  Shachar
2005/0107679 A1  5/2005  Geiger et al.
2005/0107688 A1  5/2005  Strommer

OTHER PUBLICATIONS

The geometrical representation of path planning problems; Leo Dorst, Indur Mandhyan, Karen I. Trovato invited paper in: Robotics and Autonomous Systems, Elsevier, vol. 7, 1991, pp. 181-195.*

Webster III, R.J., et al., "Nonholonomic Modeling of Needle Steering", International Symposium of Experimental Robotics, Singapore, Jun. 2004, pp. 1-10.

Webster III, R.J., et al., "Design Considerations for Robotic Needle Steering", IEEE International Conference on Robotics and Automation, Barcelona, Apr. 2005, pp. 3588-3594.

Translation of Mar. 3, 2012 Office action, Japanese Patent Application No. 2008-535158, pp. 1-17.

Translation of Jun. 28, 2012 Office action, Japanese Patent Application No. 2008-535158, pp. 1-2.

Translation of Japanese Patent Application Publication H11-120327, pp. 1-3.

Translation of Japanese Patent Application Publication 2005-131319, pp. 1-33.

Claims of PCT/IB2006/053672 (which were translated into Japanese for filing of Japanese Patent Application No. 2008-535158), pp. 1-6.

* cited by examiner

```
// STEP 1: make the straight entry
    for(t=1,entry=0; entry < MAX_THREAD_ENTRY ; t++, entry++ ){
        //t is the number of steps away - linearly.
        nominal[0][entry].n.x=t;
        nominal[0][entry].n.y=0;
        nominal[0][entry].n.s=0;
        nominal[0][entry].alpha =0;
        nominal[0][entry].theta = 0;
        nominal[0][entry].phi = 0;

// point along the x axis.
        nominal[0][entry].cost=t*weight(STRAIGHT);
            //multiply by weight. Bronchoscope=1. For Catheter example:
            // Straight neighbors not used, since they are so
            // undesirable. Could also set weight very high
    }

//STEP 2: create a 90 degree arc of points derived from evenly
//              discretized angles. NOTE: t is an angle
    for(t=3*PI/2 + angle_increment,entry=0;t<=PI*2;t+=angle_increment,entry++){
        for(i=1;i < TOTAL_THREADS;i++){
            // arc threads are numbered 1..(TOTAL_THREADS-1)
            nominal[i][entry].n.x=radius*cos(t);
            nominal[i][entry].n.y=radius*(1+sin(t));
            // Shifting the sine curve up so it runs from 0 to 1,
            // starting slowly
            nominal[i][entry].n.s= 0;

rotation_of_this_thread = (2*PI/NUM_ARC_THREADS)*(i-1);
            nominal[i][entry].n =
                    rotateX(nominal[i][entry].n,rotation_of_this_thread);

alpha = (entry+1) * angle_increment;

nominal[i][entry].cost= alpha *radius * weight(radius);
            // arclength = radius * theta(in radians) * weight
            // weight is calculated for this particular radius.
            // typically 1 if bronchoscope.
            //Varies from 1 to a high number for catheter nominal[i][entry].alpha = alpha;
            nominal[i][entry].theta = alpha * sin(rotation_of_this_thread);
            nominal[i][entry].phi = alpha * cos(rotation_of_this_thread);
                // sweep that t has taken = tangent (offset angle)
        }
    }
```

FIG. 6

```
POINT_STRUCT rotateX(POINT_STRUCT a, double theta)
// rotations are continuous, returning a double
{
        POINT_STRUCT  returned_point;

returned_point.x=a.x;
        // x' = x
        returned_point.y=cos(theta)*a.y - sin(theta)*a.s;
        //     y' = y*cos q - z*sin q
        returned_point.s= sin(theta)*a.y + cos(theta)*a.s;
        // z' = y*sin q + z*cos q
        return returned_point;
}

POINT_STRUCT rotateY(POINT_STRUCT  a, double theta)
// rotations are continuous, returning a double
{
        POINT_STRUCT returned_point;

returned_point.x=sin(theta)*a.s + cos(theta)*a.x;
        // x' = z*sin q + x*cos q
        returned_point.y=a.y; // y' = y
        returned_point.s=cos(theta)*a.s-sin(theta)*a.x;
        // z' = z*cos q - x*sin q
        return returned_point;
}

POINT_STRUCT rotateZ(POINT_STRUCT a, double theta)
// rotations are continuous, returning a double
{
        POINT_STRUCT returned_point;

returned_point.x=cos(theta)*a.x-sin(theta)*a.y;
        // x' = x*cos q - y*sin q
        returned_point.y= sin(theta)*a.x+cos(theta)*a.y;
        // y' = x*sin q + y*cos q
        returned_point.s=a.s;
        // z' = z
        return returned_point;
}
```

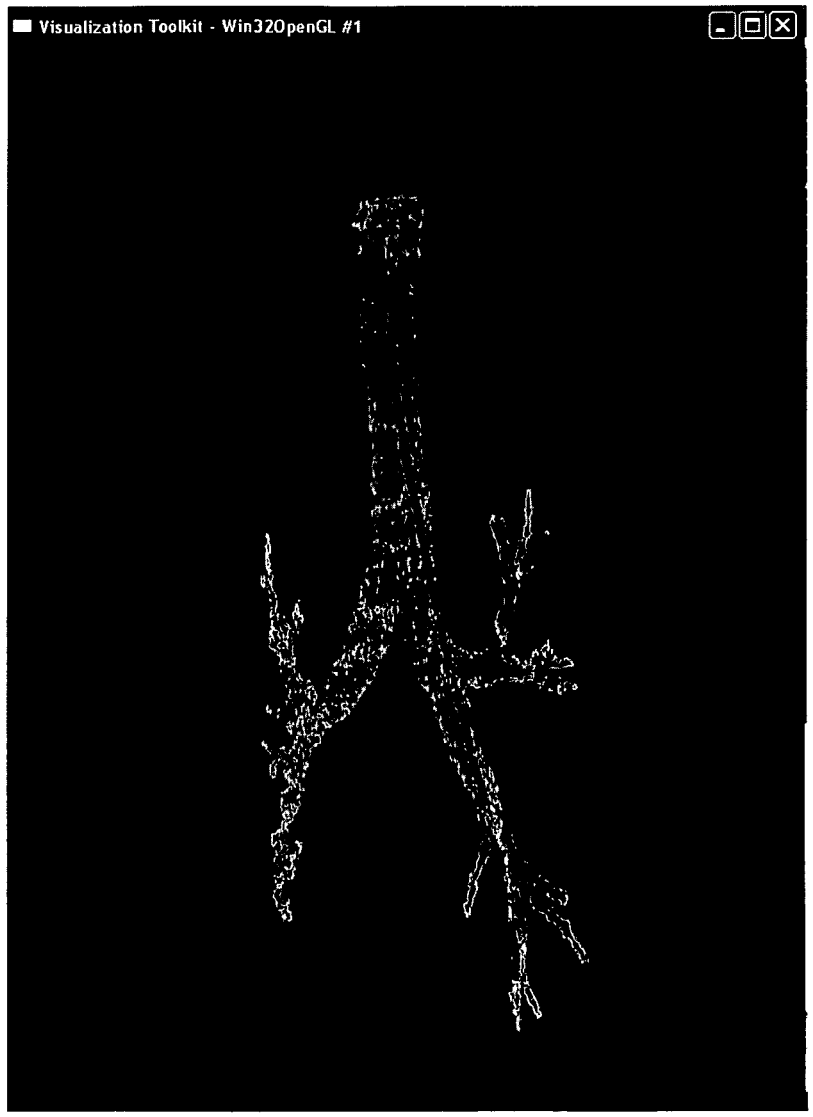
FIG. 9               900

3D TOOL PATH PLANNING, SIMULATION AND CONTROL SYSTEM

CROSS REFERENCE TO RELATED APPLICATIONS

This application claims the benefit of international Application Number PCT/IB2006/053672, filed Oct. 6, 2006, and U.S. Provisional Application Ser. No. 60/725,185 filed Oct. 11, 2005 which are incorporated herein in whole by reference.

The present invention relates to a system, apparatus and method for planning a tool path in a patient.

Catheters are used to position other devices for balloon angioplasty, stenting, and tumor ablations. Today a catheter is maneuvered using visual feedback, often by 'live x-ray' also called fluoroscopy.

Catheters come in many shapes and sizes with different flexibility. They are chosen for the procedure based on a surgeon's judgment, or sometimes based on statistical norms for the procedure.

U.S. Pat. No. 6,726,675, entitled "Remote control catheterization", assigned to Navicath Corporation discloses a system that enables the automated control of catheters, which automatically feeds the catheter forward, as well as rotates it.

The manual control of catheters requires practice, dexterity, the ability to interpret position based on fluoroscopy (a projection) and the time of expensive experts. Further, patient specific simulations based on morphological data are not readily available. Selection of a catheter is not performed based on patient morphology, but on the experience of the surgeon and statistical norms. This may lead to unnecessary delay and complications in some procedures.

For a lung CT, there are about $3\times10^{12}$ elements required to represent the position and orientation of a catheter's tip. This is 60-120 terabytes of RAM, making it intractable on today's computers.

There are many choices of catheter for the surgeon, but they may be selected based on statistical norms, rather than patient specific morphology. This non-optimal choice can slow the procedure or increase the risk to the patient.

Regarding scope technology, today, a bronchoscope is used to examine deep areas of the lung, and an endoscope is used to enter natural body cavities such as either end of the GI tract or through small incisions such as in laparoscopic procedures. Colonoscopes and sigmoidoscopes are types of endoscopes. The scope is maneuvered for visual inspection, diagnosis, often through biopsy, as well as to deliver some forms of therapy such as Photodynamic therapy.

The manual control of a bronchoscope requires practice, careful manual control and the time of expensive experts. Further, patient specific-simulations are not readily available.

Techniques used for robot control or vehicle control are non-obviously applicable to controlling a catheter and a scope. A configuration space in the art in particular, is considered to be the set of all poses representing the possible states of the tool. For a bronchoscope, this is a 6 dimensional problem, including the 3D location and 3D orientation.

For a lung CT, there are about 512×512×240 (X×Y×slices), or 62,914,560 locations. The angles can be coarsely discretized at each 10 degrees in rX, rY and rZ (also called roll, pitch, and yaw). Even at this coarse discretization, the configuration space would require:

512×512×240×36×36×36=2,935,341,711,360 elements (about $3\times10^{12}$).

Since each element contains between 20 and 30 bytes, this is 60-120 terabytes just for the configuration space, which is ideally stored in RAM for fastest access. The storage requirements for today's computers make this alone a difficult task.

The system, apparatus and method of the present invention reduce the configuration from 6 degrees of freedom to 3, by using the locations as states and storing the r (roll), p (pitch), w (yaw) angles that provide the orientation setting at the current state and by generating neighborhoods that are used to maintain kinematically correct angles of the catheter's and scope's tip from any orientation. This makes the calculation tractable in today's systems, and always faster in tomorrow's computing systems. The resulting path is kinematically correct (i.e. achievable with a given tool), collision-free and optimal in the discretized space. Using this method, a plan is generated for a bronchoscope to travel through the lungs to a target location such as for biopsy, and a plan for catheter motion is achieved through the blood vessels.

Embodiments of the present invention are a non-obvious variation of the path planning technologies described in U.S. Pat. No. 6,604,005 to L. Dorst & K. Trovato and in "Method and apparatus for controlling maneuvers of a vehicle," U.S. Pat. No. 5,870,303 to K. Trovato and L. Dorst, Feb. 9, 1999.

For a catheter, a neighborhood contains all possible motions that a catheter can make. These are insertion (fwd motion), left and right turn (rotation), with costs weighted by the strain induced by following various turns and catheter rotation.

For a scope, a neighborhood contains all possible motions that a 'scope' can make which are insertion (fwd motion), left turn and right turn (rotation) for a given maximum turning radius which may vary in each direction, with costs based on the distance traveled.

Key differences from prior work include:

For all tools: 6D in 3D configuration space, by storing the resulting orientations inside the 3D space.

Catheters, bronchoscopes and beveled needles, behave as a car does, i.e. non-holonomically.

Neighborhood is different: comprises 3D with threads in many orientations, not a single surface, like a car.

Bronchoscope control is different from car control: has Up/Down, Left/Right, Forward, and all combinations as well as gradations.

Catheter control is different from car control: catheter has alpha rotation and Forward only.

Beveled Needle control is different from car control: has a single "turning radius", but the rotation of the needle can allow it to move off in different directions, whereas prior art teaches turning in a 2 dimensional environment, i.e., a plane, since control was only for the needle at 0 or 180 degrees.

FIG. 6 illustrates software to generate a line and arc of a nominal neighborhood of a bronchoscope, as well as the rotation of each of the arcs to form the different threads;

FIG. 8 illustrates software to accomplish rotations of the points;

FIG. 9 illustrates a path for a bronchoscope through the trachea and bronchi;

Figure 1:
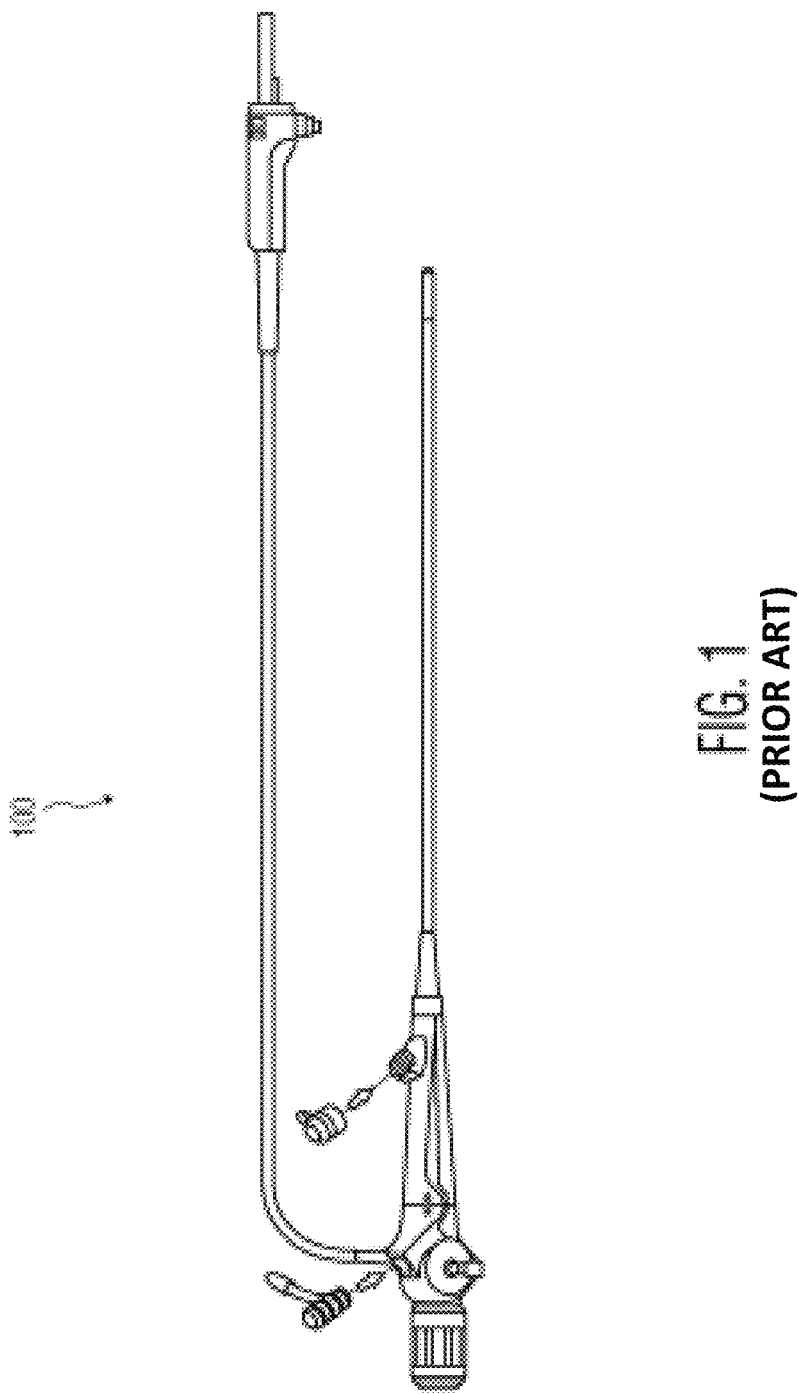
FIG. 1 illustrates a bronchoscope.

It is to be understood by persons of ordinary skill in the art that the following descriptions are provided for purposes of illustration and not for limitation. An artisan understands that there are many variations that lie within the spirit of the invention and the scope of the appended claims. Unnecessary detail of known functions and operations may be omitted from the current description so as not to obscure the present invention.

Path Planning for a tool or 'autonomous system' can be performed using the framework taught by K. I. Trovato, *A\* Planning in Discrete Configuration Spaces of Autonomous System*, University of Amsterdam, 1996. Each of the components of the framework is described below. Once the components are known, they can be used within a cost wave propagation method to generate a path. The required components of the framework are then described for a bronchoscope, catheter, and beveled needle.

Framework

Configuration Space/System Status

The tool or autonomous system must be able to be described in discretized form. That is, the tool is characterized by key properties (or parameters), each property having one or more ranges of valid discrete values. A tool status, therefore, provides a unique setting for each of these properties. The span of all the possible parameter ranges is called the configuration space, abbreviated CS. Sometimes the configuration space matches the 'task space' or environment in which the actions are carried out.

Nodes/States/Events/Transitions

Since it is a discretized space, the status or 'pose' of the tool can be considered as 'nodes' in a graph. Additionally, any events in the system that can cause a change between one system state and another can be viewed as 'transitions' between the nodes.

Criterion/Cost

The objective of the tool often has a criterion for success, such as fastest, shortest, least expensive, etc. In many cases, this can be directly translated to a cost incurred for a particular transition between nodes. The set of nodes, transitions and costs forms a configuration space graph.

Atomic Actions/Neighborhood/Successors

The allowed atomic actions that cause changes or transitions from one state in the configuration space to another in a certain range are encapsulated as the "neighborhood." This neighborhood is a collection of permissible successors. The permissible successors represent the core capability of a tool to make certain motions. Because this usually does not vary based on location, for efficiency the neighborhood can be defined once, and used relative to any original state. The neighbors also may be determined based upon 'rules of the game', so there may be a few neighbors that are selected by a particular attribute of the controlled tool.

Assigned to each transition is the cost imposed for changing between an original state and a neighbor state. Therefore the combination of the states in configuration space with the transitions between them can be thought of as a graph with the states as nodes and permissible transitions as directed edges.

Constraints/Forbidden Regions/Obstacles

For many applications, the tool has constraints. The latter define illegal tool states, often because of mechanical limits, interaction with the environment (i.e. obstacles), or imposed rules. These must be transformed into forbidden regions of nodes in the configuration space. In some graphs, the transitions into these nodes are removed along with the nodes themselves. Alternatively, the nodes may be marked as illegal, or transitions into the node may have infinite (unattainable and high) cost, denoted by $\infty$. Each of these techniques causes a search to avoid the constrained nodes.

'goal'/'start'

The tool 'goal' position may be mapped to one or more equivalent 'goal' nodes in the discretized configuration space. Multiple 'goal' nodes may exist because the formulation of parameters expressing the system may have more than one solution describing the system 'goal'. (For example both left handed and right handed configurations of your arm can reach the same location.) The system 'start' is simply transformed to a specific 'start'ing node.

Series of Events/Optimal Path

Finding the most desirable series of events leading from a current system node to a desired 'goal' is analogous to finding an optimal path of transitions from the current node to the 'goal' node that incurs a minimum cost while avoiding all illegal nodes. This desirable series of events therefore can be found by planning a path using the configuration space nodes, transitions, costs, forbidden regions, and 'goal', and by knowing a 'start'ing node. A graph search method such as A* provides an efficient mechanism to determine the path. Once the components are in place, the A* algorithm can be used to compute solutions.

Bronchoscope Embodiment (B)

FIG. 1 shows a bronchoscope. In a preferred embodiment, a bronchoscope has the following framework components:

B.1 Configuration Space

Figure 2:
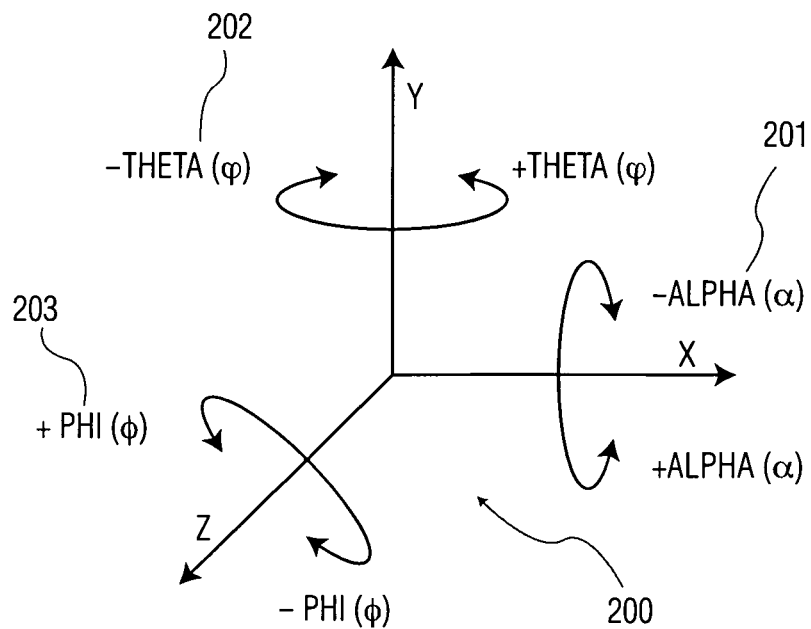
FIG. 2 illustrates a 3D configuration space (200) having configurations at each location in the discretized X, Y and Z directions.

In a preferred embodiment, the configuration space of a bronchoscope is represented as the location of the tip of the bronchoscope in 3 space, as shown in FIG. 2. The orientation of the tip is described in terms of rotations about the X, Y, and Z axes, called alpha 201, theta 202 and phi 203 respectively. There is a positive direction for each angle, and negative direction for each angle. Our example uses a standard 'right hand rule' system to identify the axes and relative orientations, however others could be used. The 'start', 'goal' and permissible region of travel can be imaged using CT, MRI or 3D ultrasound (3D electronic or synthetic), and used as a basis to size the configuration space. The tip also has an orientation which requires 3 additional angles, see FIG. 2. In the prior art, each angle would have to be discretized in each of the 3 positions and orientations, creating a 6 dimensional problem. The paths can be computed in this space; however, this makes an already large data set much larger.

The concept of a configuration space results in a definition that spans all parameters characterizing a tool pose thereby resulting in an immense configuration space. For example, a lung image having 512×512 pixels and 295 slices, with 360 possible discretized angles for each of the 2 orientations becomes a volume of 512×512×295×360×360, or 10,022,289,408,000 states.

For 3 orientations, the volume is

512×512×295×360×360×360 states or 3,608,024,186,880,000.

Coarser discretization reduces the set of orientations, but adds errors. Further, these ultra-large volumes of data exceed many current computing capabilities.

Current 32-bit hardware and operating systems limit RAM per process to 2Gigabytes, making memory limitations a serious problem for medical imaging. 64-bit hardware and operating systems will relieve some of these difficulties; however the methods for reducing space will continue to be useful.

B.2 Minimizing Configuration Space

To convert this apparent '6D' problem to a more manageable size, several observations are noted:

There is only one orientation of the tool tip that is optimal along any particular path in configuration space. It can therefore be sufficient to store only one option in each positional configuration state (i.e., x, y, z), which converts the problem to 3 Dimensions, requiring storage O(CT volume). This dramatically reduces the size of the configuration space, by a factor of over 46.6 million (360×360×360).

In addition, rather than discretizing the angles, which would be required previously, the values stored in the configuration space can be integers, floats or doubles to represent arbitrarily precise angles. The discretization error of the angles can be greatly reduced this way.

Finally, the 6 dimensional planning can be encapsulated in the calculation of a nominal neighborhood, which can reduce the calculation overhead further.

This reduction in volume is possible since the angles are used for two purposes that do not require independent states:
1) as a characteristic within the x, y, z location to help orient a successive expansion of the space; and
2) as a determinant of the control parameters as a path is being followed.

B.3 Nodes and Transitions

At each location in the configuration space a node data structure holds key information. The following is a preferred space node data structure of the configuration for a bronchoscope:

```
float cost_to_goal;
struct csnode *best_parent_ptr;
unsigned int heap_location; //index into heap (tree[i])
float alpha, theta, phi; // rotation about x,y,z
short thread_number; // optional. Infers radius and orientation.
``` where:
cost_to_goal stores the value of the cost from the current node to the nearest 'goal' and is updated when the A* (or Differential A*) method re-computed the space.
Best_parent_pointer points to one 'equivalent' parent because the number of potential neighbors can exceed 32 or 64, making it more space efficient to store the address directly and in a preferred embodiment is a pointer to the first low cost parent.

A heap is used in a preferred embodiment to keep track of the nodes yet to be expanded. This is a different storage structure than the configuration space. In order to manage the changing values in the heap in an environment where costs may increase or decrease quickly during the search, location links between the configuration space and the heap are included. The heap has a link to the configuration space node and the configuration space has a link back to the heap. These links are updated as the heap is adjusted.

In an alternative embodiment, the configuration state comprises the number of the thread used to travel from the parent node to the (current) neighbor node. From this thread a radius and orientation of the current node can be determined and used to control the device. This eliminates the re-computation of this value during actual path following. In a real-time control situation however, the 'on the fly' re-computation of the thread may be desirable if the arc can vary slightly to compensate for the difference between the plan and the live environment, which includes breathing or body motion.

Since it is possible that no path exists, a pre-determined algorithm is used to determine whether or not a path exists. If the path exists, the algorithm generates a series of nodes from a node n to the seed node (often the goal). An example of such an algorithm is:

```
follow_path_from (n)
{
if(best_parent != NULL) // there is a path
    While (n != seed) // haven't arrived yet
    {
        append_to_path(n)
        n = n.best_parent // follow along to next node in series
    }
    if (n == seed) // either arrived at seed, or started there
        append_to_path(n)
else // best_parent was null, that is, there was no path from n to seed
    printf("No path from n to seed");
}
```

B.4 Criterion/Cost

For the bronchoscope embodiment, the minimum distance of the bronchoscope tip will be the optimization criterion. Therefore, the distance that the tip travels is measured by the arc struck by the curvature defined by the 'turning radius' (straight or turned). It is calculated for each nominal neighbor in the next section. Clearly, other criteria might be used, such as those that are weighted near the borders of the bronchi to encourage safer paths.

B.5 Atomic Actions/Neighborhood/Successors

Figure 3:
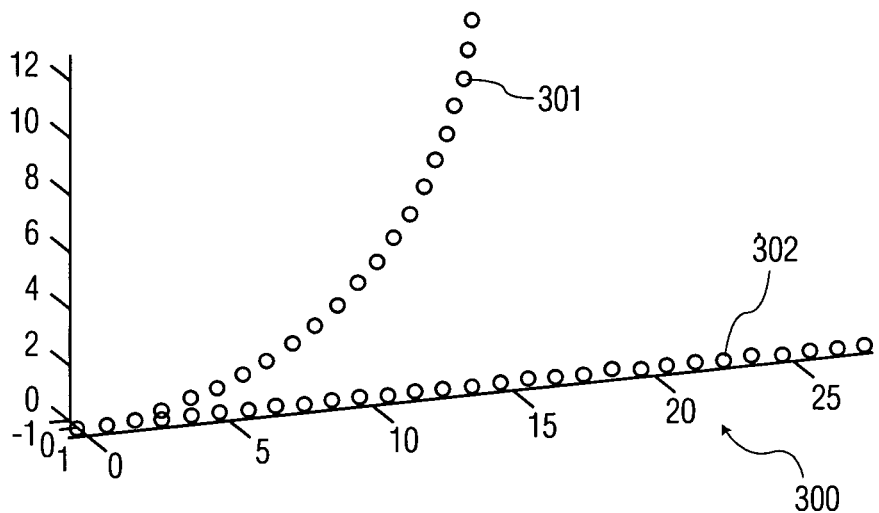
FIG. 3 illustrates a part of a neighborhood of a bronchoscope.

The bronchoscope's tip has a few basic capabilities. It can be set straight, turn right/left or turn up/down. As the bronchoscope advances, the later scope body follows the path set by the tip. Referring now to FIG. 3, part of the neighborhood is illustrated, showing the set of possible straight motions along a small unit direction (e.g. X) 301. Each arc, including the straight line 301, is called a thread. The notion of a thread denotes the precedence of visitable points. In other words, the points farther from the home position cannot be reached if an intervening point is blocked (e.g. costs infinity). The arc generated that sweeps into the Y direction is also calculated and shown 302. The arcs are about a 90 degree sweep into a circle having the turning radius specified. Ninety (90) degrees is the maximum required. The number of neighbors is therefore related to the size of the radius. That is, larger radii require more neighbors to cover the full 90 degree arc.

This arc is then rotated about X for an arbitrary number of degrees, evenly distributed. Therefore, the thread number implies a particular turning radius (infinity, if the angle is straight) and rotation about X relative to the current orientation.

Figure 4:
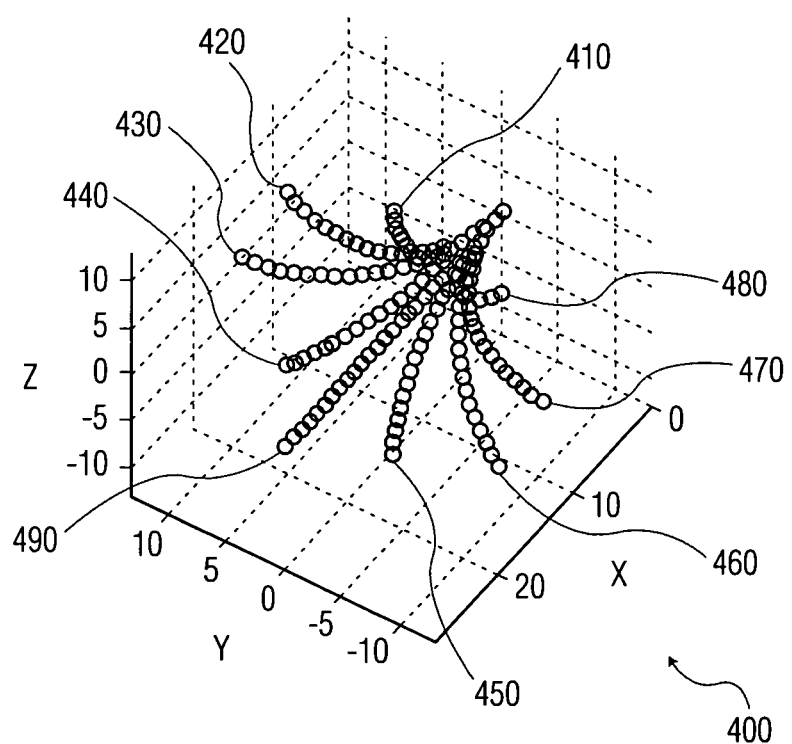
FIG. 4 illustrates a nominal neighborhood describing basic capabilities of a bronchoscope.

An example of datapoints and values for a nominal neighborhood describing the basic capabilities of a bronchoscope is given in FIG. 4. This nominal neighborhood identifies the relative locations in X, Y and Z for each neighbor from a default (i.e., (0, 0, 0) orientation of alpha, theta and phi). An example of the data for this neighborhood is presented in Appendix A.

Figure 5:
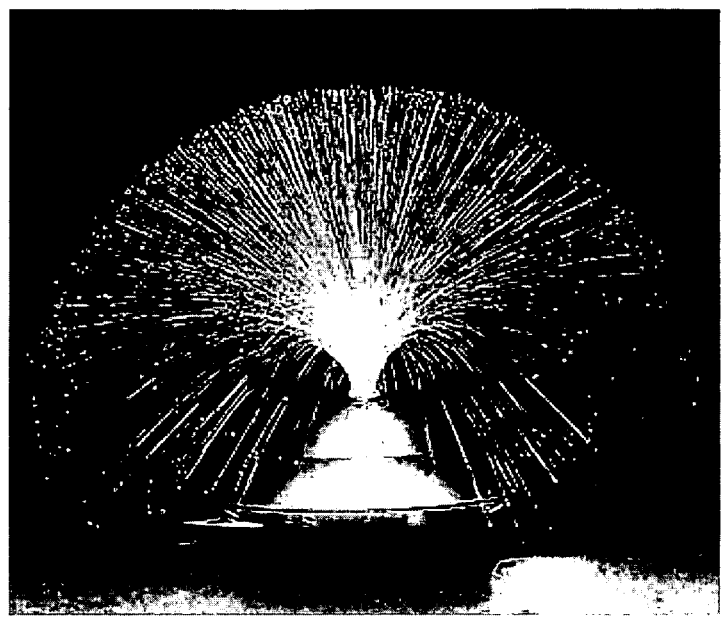
FIG. 5 illustrates an analogous 3D neighborhood of a bronchoscope including a plurality of radii.

As a logical extension, in a preferred embodiment, the neighborhood includes many possible radii, to cover a greater volume of the 3D region. This neighborhood would be calculated in 3D as is shown by the analogous shape of FIG. 5, being similar to the group of threads in a thread/fiber optic lamp. So, every state in the volume is to be filled. This is really an analogy. Tighter turning radius threads are shorter, and longer turning radius threads are longer. This could be performed, however experience shows that only the extreme control capabilities and "straight" are actually used. Therefore, reducing the number of neighbors to those that are actually used reduces the computation time needed. Where the cost measure is not distance, but more complex, these neighbors may become essential. An example of a complex metric might be one that minimizes distance from the edges of the tubes (bronchi, bloodvessels or freespace). In this case, precise curvature may be more essential.

An example of the software code to generate the line and arcs of the nominal neighborhood is provided in FIG. 6.

Assume that the nominal neighborhood is calculated once, at startup.

B.6 Constraints/Forbidden Regions/Obstacles

The input to the present invention includes a segmented 3D image, such as from a CT. This defines the free-space regions (i.e. where motion is permitted) and illegal regions of tissue. The free-space nodes are set to 'uncosted', meaning that they are free to be updated. The illegal regions are set to 'infinity', a special (high) value which is also an indication that the path may not pass through.

B.7 'goal'/'start'

There are a few ways that the notions of 'start' and 'goal' can be used. In reality, the path can be calculated starting in either direction, taking care to calculate properly any directional costs. For example, driving backwards the wrong way along a one-way street is not permitted.

The 'goal' may be the 3D location of a tumor in the lung, which is used as a 'seed' node for the search. The approach orientation may also be proposed by the doctor, such as if a biopsy is to be obtained from a tool fed through to the tip of the bronchoscope. In this case, the 'start' node is not absolutely required.

The 'start' node may also be a 'seed' node, which is often located at the approximate center of the trachea. This location is easy to select graphically on a lung CT, since it is a large black circle on the first (or last) slice of the volume. In this case, the 'goal' node is not absolutely required.

In the 3D configuration space, having a single orientation per node, the 'seed' node must have a defined orientation. In a case where multiple orientations are possible, the plan may be regenerated from the 'seed' node using different orientations. In many clinical cases however, an orientation can be defined relatively easily. For example, a tumor may be entered from one of several points on its surface, but is ideally biopsied from an orientation normal to the surface. Each surface location in the configuration space may thus have an ideal orientation.

B.8 Series of Events/Optimal Path

Figure 7:
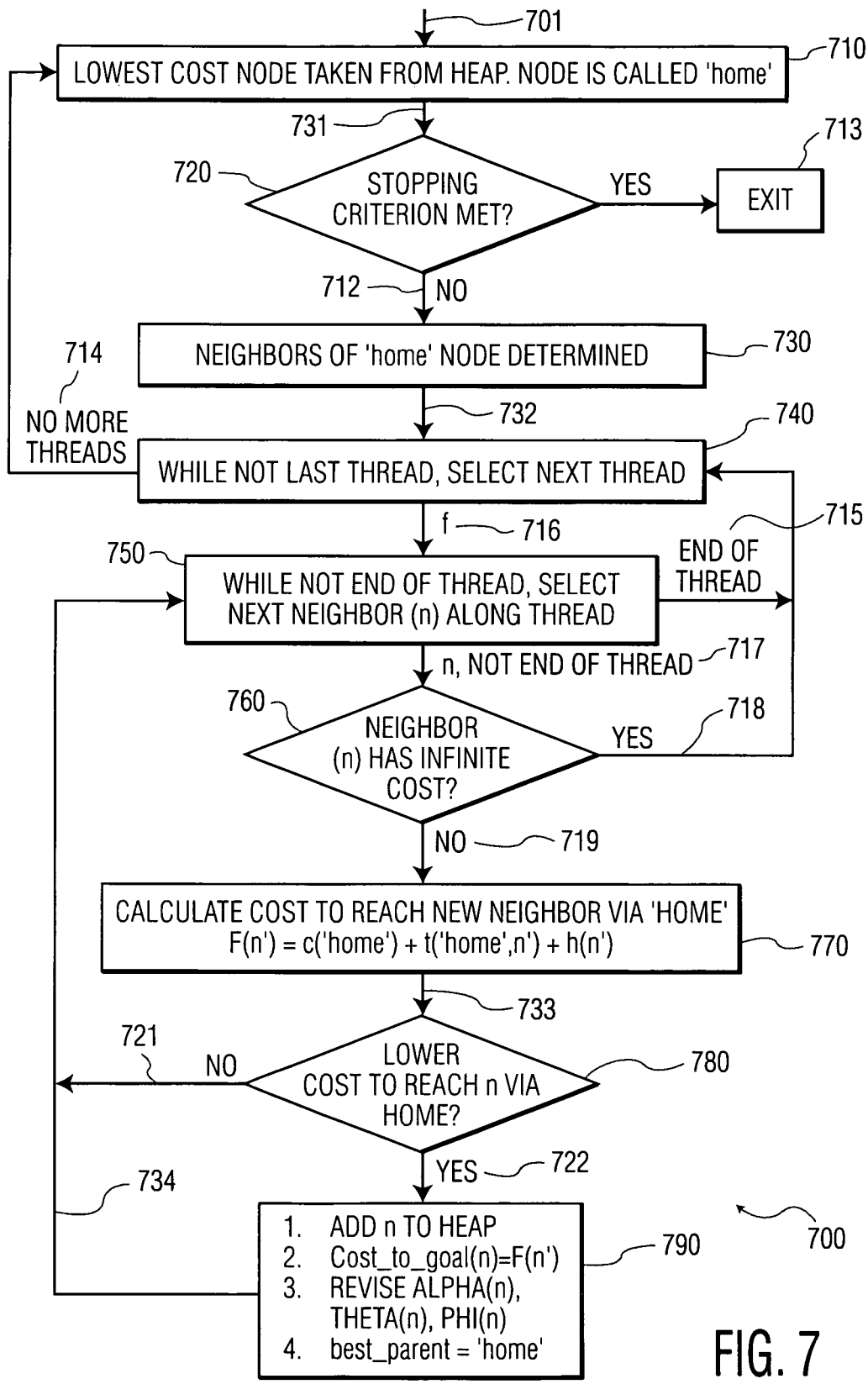
FIG. 7 illustrates a flow diagram of the A* algorithm for determination of an optimal path from a 'seed node' to a 'goal', which is customized to manage the neighborhood thread by thread, including the precedence of neighbors.

A 'seed' node is placed into the heap in order to begin cost wave propagation, or A*. The heap is a balanced binary tree that maintains the lowest cost value at the root. The steps in FIG. 7 are taken.

The process begins with 701, leading to step 710. In step 710, the lowest cost node is taken from the heap. The node taken from the heap is called 'home'. It is assumed that well-known algorithms are employed to ensure that the heap remains correct. The process passes to step 720 via 731.

In step 720, the "stopping criterion" is tested. There are many tests that can be performed to determine if the process may stop. The "stopping criterion" may include, for example:
1. Heap empty
2. Current ('home') node's cost_to_goal value is greater than the (non-'seed') 'start' or 'goal'. This enables the search to terminate before the entire space is filled; however, it does give the optimal path between the 'start' and 'goal'.

If the 'stopping criterion' is met, the process exits at step 713 by following arrow 711. If the "stopping criterion" is not met, then the process passes to step 730 via 712.

In step 730, the neighborhood of permissible motions is generated. The neighbors of the 'home' node are calculated based on the 'home' node's orientations given by its alpha, theta and phi as well as its 'home' x, y, z location. The neighborhood results from rotating the nominal neighborhood by alpha, theta and phi, and then translating the already rotated neighborhood relative to the 'home' node's x, y, z location. Methods for rotation and translation of points are well known to those skilled in the art; however, an example of the software code to accomplish these transformations is provided in FIG. 8.

In the case where a pixel is not perfectly square, such as in CT images, where the ratio of x:y:z may be 1:1:1.3 for example, the rotations are performed, and then the values are scaled. The resulting neighborhood is then translated to the location of the current expanding node. Once the neighbors for the current 'home' node are computed, the process passes to step 740 via 732.

In step 740, the next thread of the neighborhood is chosen. If there are no more threads, then the process passes back to 710 via 714. If there is a thread (f), then the process passes to step 750 via 716.

In step 750, the next neighbor (n) along the thread (f) is chosen. If there are no more neighbors along this thread, then the process passes back to 740 via 715. If there is another neighbor (n), then the process passes to step 760 via 817.

In step 760, the cost value of the neighbor is tested. If it is infinite, or there is another indication that the neighbor is not passable, the process passes back to 740 via 718. Another indication might be that the neighbor has a cost value higher than some pre-determined threshold, which is less than infinity, but too high to pass. This threshold may be a function of the current distance traveled (at the 'home' node), for example. If the neighbor does not have infinite cost, the process passes to step 770 via 719.

In step 770, the proposed new cost, F(n') is calculated for the new neighbor. Since the neighbor may already have a cost, it is denoted F(n'). In the A* algorithm, a heuristic h(n) may be used to guide the search. A perfectly valid value is h=0, however, which causes the space to fill from all 'seed' nodes until the 'stopping criterion' is satisfied/true. The process then passes to step 780 via 733.

In step 780, the calculated cost F(n') is compared with the pre-existing cost at n, F(n). If F(n') is greater than F(n), then it is more costly to reach n via the 'home' node than whatever was determined previously, and the process returns to step

750 via 721. If the calculated cost F(n') is less than F(n), then this value is an improvement over prior directions. In this case, the process passes to 790 via 722.

In step 790, the node is added to the heap. If it is already on the heap, then the value is updated and the heap adjusted. The new cost_to_goal is assigned to n, as is a new alpha, theta and phi. The values of alpha, theta and phi are calculated by adding the values of the nominal node's alpha, theta and phi to the parent's alpha, theta and phi. The revised 'best_parent' leading the best way to the 'seed' node, is assigned 'home'. Optionally, but preferably, the number of the thread is stored. This minimizes computation later on during path following, since the number of the thread maps directly to the control parameters, that is the amount that the scope is turned up/down and left/right.

B.9 Variations

If there is likely to be either control or sensory error, it is preferable to define the neighborhood more narrowly than theoretically possible. For example, the turning radius is increased beyond the smallest possible. This may compensate for unexpected control or sensing errors by a slight over correction during the procedure.

The bronchoscope may not be symmetric. That is, the radius of curvature in the left, right, up, down directions may not be equal.

B.10 Path Following

After the search completes in FIG. 7, step 713, several processes can occur, in a preferred embodiment.

If a 'start' and 'goal' are identified, then the path can be rendered, or carried out by sending setpoint to the instrument, giving the advancement distance, and the angles for the right/left and up/down controls. These values can be determined either by calculating the optimal arc between the current position and orientation and the target position and orientation. In the preferred embodiment, the thread number (such as from step 790 of FIG. 7) or curvature and angle are stored so that the correct right/left, up/down settings are achieved.

In an alternative embodiment, if the 'start' node is the 'seed' node, then the 'goal' node is 'picked' by the physician by showing the reachable states in 3 space. The physician then picks a target location, such as the location of a tumor. Alternatively, a Computer Aided Detection system highlights suspected lesions as a subset of points, and the physician more picks a target location from this subset of points.

In a further alternative embodiment, if the 'goal' node is the 'seed' node, then the bronchoscope is tracked in real-time. The x, y, z location of the tip of the bronchoscope is used to look up the matching location in the configuration space. Based on the location of the scope's tip, the angle of the tip is adjusted to the proper L/R, U/D angles.

An example path is illustrated in FIG. 9, where the path 901 is shown through translucent lung states. When the path moves along the edge of the bronchial tree, the path 901 is brighter since there are no translucent pixels between the path and the view.

The bronchoscope has two controls, plus the ability to advance into the patient. The controls are 'Left, Center, Right' on one dial, and 'Up, Level, Down' on the other dial. The Center is between Left and Right, and Level is between Up and Down. Advancement is performed by hand or can be performed with a machine. The path is followed from the 'start' to the 'goal', reading out each 'setpoint' in turn from the configuration space. The setpoints give the current location and orientation, the amount to advance to reach the next setpoint, and the thread number. The thread number gives the pose that the bronchoscope should have in order to reach the next setpoint. In FIG. 4, there are 9 threads. One is straight, and the others perform a 14 mm turning radius arc. Preferably, the thread number is stored, although the controlled pose can be calculated as the largest radius arc leading from the current location to the 'goal' location and orientation. This 'on the fly' computation can also be useful to manage real-time deviations in control or patient motion. The threads shown in FIG. 4 correspond to the actions in Table 1:

TABLE 1

| Thread # | Left/Right Control | Up/Down Control |
|---|---|---|
| 410 | Center | Up |
| 420 | Right | Up |
| 430 | Right | Level |
| 440 | Right | Down |
| 450 | Center | Down |
| 460 | Left | Down |
| 470 | Left | Level |
| 480 | Left | Up |
| 490 | Center | Level |

Catheter Embodiment (C)

Figure 10:
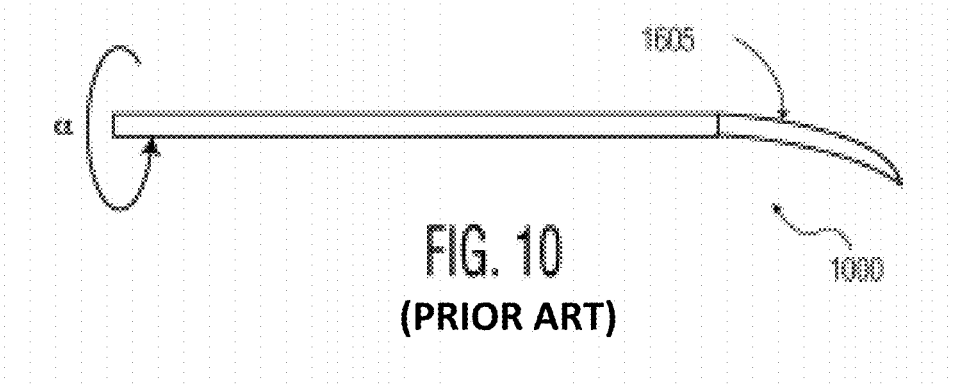
FIG. 10 illustrates a catheter.
Figure 11:
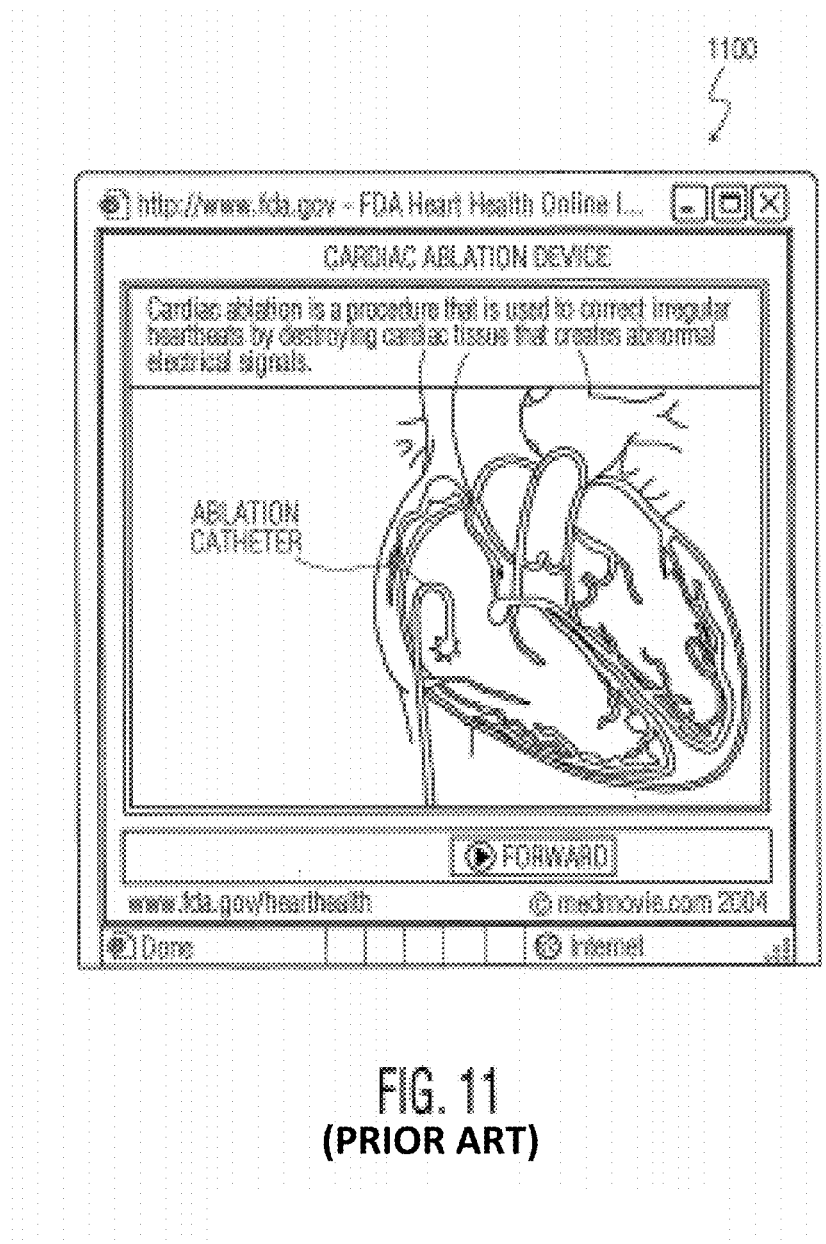
FIG. 11 illustrates a catheter that has been manually positioned for cardiac ablation.

A catheter is used to perform actions at a distal location within vasculature. Examples of such procedures are angioplasty and cardiac catheterization. Cardiac procedures use catheters fed from the femoral artery up to the heart, although sometimes access to the heart is via arteries of the arm or wrist. An example catheter is shown in FIG. 10. Another use of catheters is for cardiac ablation, where heart rhythm can be restored by selectively ablating improper electrical paths of the heart. FIG. 11, from the FDA website (www.fda.gov), illustrates how an ablation catheter 1101 is used in the heart, according to the prior art, where the catheter is manually controlled under image guidance. Since there is no automated control available for cardiac catheter control in the prior art, the procedure can take hours until the proper location in the heart vessels is achieved.

C.1 Configuration Space

In a preferred embodiment, the configuration space of the catheter is represented as the catheter tip's location in 3 space. The 'start', 'goal' and permissible region of travel can be imaged using CT, MRI or 3D ultrasound (3D electronic or synthetic), and used as a basis to size the configuration space. The tip also has an orientation requiring 3 additional angles, such as those shown in FIG. 2.

In the prior art, each angle is discretized in each of the 3 dimensions. The paths can be computed in this space; however, this makes an already large data set much larger. For a lung image having 512×512 pixels and 295 slices, with 360 possible discretized angles for each of the 3 orientations, the volume is $$512\times512\times295\times360\times360\times360 \text{ nodes or } 3{,}608{,}024{,}186{,}880{,}000 \text{ nodes.}$$

Coarser discretization reduces the set of orientations, but adds error. Further, these ultra-large volumes of data exceed many current computing capabilities, having the same problems with current hardware.

C.2 Minimizing Configuration Space

To convert this apparently '6D' configuration space problem to a more manageable size, a few observations are made:

There is only one orientation of the tool tip that is optimal along any particular path in configuration space. It can therefore be sufficient to store only one option in each positional configuration state (i.e., x, y, z), which converts the problem to 3 Dimensions, requiring storage $O$(CT volume). This dramatically reduces the size of the configuration space, by a factor of over 46.6 million (360×360×360).

In addition, rather than discretizing the angles, which would be required previously, the values stored in the configuration space can be integers, floats or doubles to represent arbitrarily precise angles. The discretization error can then be greatly reduced.

Finally, the 6 dimensional planning is encapsulated in the calculation of a nominal neighborhood, which reduces the calculation overhead further.

This reduction in volume is possible since the angles are used for two purposes that do not require independent states:

1) as a characteristic within the x, y, z location to help orient the successive expansion and
2) as a determinant of the control parameters as a path is being followed.

c.3 Nodes and Transitions

Just as in the bronchoscope embodiment, at each location in the configuration space of a catheter, a data structure holds necessary information. The following is a preferred configuration space node data structure for a catheter:

```
float cost_to_goal;
struct csnode *best_parent_ptr;
unsigned int heap_location; //index into heap (tree[i])
float alpha, theta, phi; // rotation about x, y, z
short neighbor_number; // optional. Can infer radius and orientation.
```

Each of these variables is described in more detail next:

cost_to_goal stores the value of the cost from the current node to the nearest 'goal' and is updated when the A* (or Differential A*) method recomputed the space.

best_parent_pointer points to one 'equivalent' parent because the number of potential neighbors can exceed 32 or 64, making it more space efficient to store the address directly and in a preferred embodiment is a pointer to the first low cost parent.

A heap is the storage data structure in a preferred embodiment. In order to manage the changing values in the heap in an environment where costs may increase or decrease quickly during the search, location links between the configuration space and the heap are included. The heap has a link to the configuration space node, and the configuration space has a link back to the heap. These links are updated as the heap is adjusted.

In an alternative embodiment, the configuration state comprises the number of the thread used to travel from the current node to the parent node. From this thread a radius and orientation of the current node can be determined. This eliminates the re-computation of this value during actual path following. In a real-time control situation however, the 'on the fly' re-computation of the thread may be desirable if the arc can vary slightly to compensate for the difference between the plan and the live environment, which includes breathing or body motion.

c.4 Criterion/Cost

Figure 12:
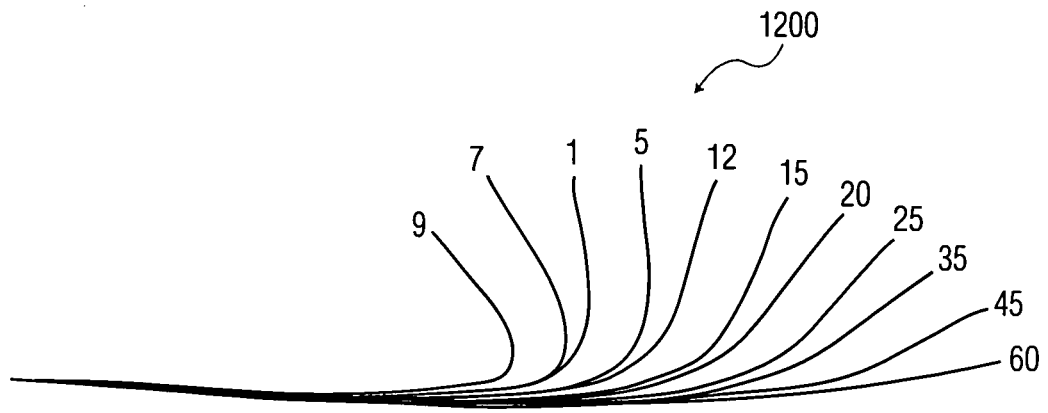
FIG. 12 illustrates weights for cost wave propagation for a catheter path planning activity according to the present invention.

For the catheter example, the easiest path is desired. Since the catheter is often flexible but curved, the catheter remains inside the walls of the vessels exerting a pressure along the walls. The objective is to minimize the pressure along the walls, both to minimize the risk of puncture by examining the peak pressure, and by minimizing the difficulty steering by using the most unstressed shapes for the traversal. The minimum deviation of curvature for the catheter tip will be the optimization criterion, however a cutoff maximum will also be imposed. To achieve this, the distance that the tip travels is weighted by the deviation from the 'normal' unstressed shape of the catheter. The weight can be proportional to the stress at the tip or can be an exponential function. For example, the weights may be as shown in FIG. 12. For simplicity of graphing, we show only two weighted arcs, one having the 28 mm radius neighbors weighted by 1, and the 14 mm radius weighted by 7.

c.5 Atomic Actions/Neighborhood/Successors

The catheter's tip has only two control capabilities. It can be rotated and it can be pushed in or out. The arcs defining the end of the catheter can be approximated by the same type of turning radius as the bronchoscope, and the same code in FIG. 13 can be used to generate the threads, however the weights are adjusted according to the metric described in the prior section. As in the bronchoscope example, the neighborhood is calculated for each 'thread'. As the catheter advances, the later catheter body follows the path set by the tip. An example of datapoints and values for a nominal neighborhood describing the basic capabilities of a catheter is given in Appendix B. This nominal neighborhood identifies the relative locations in X, Y and Z for each neighbor from a default (i.e., (0, 0, 0) orientation of alpha, theta and phi). Assume that the nominal neighborhood is calculated once, at startup. An example of the data for this neighborhood is graphed in FIG. 13.

Figure 13:
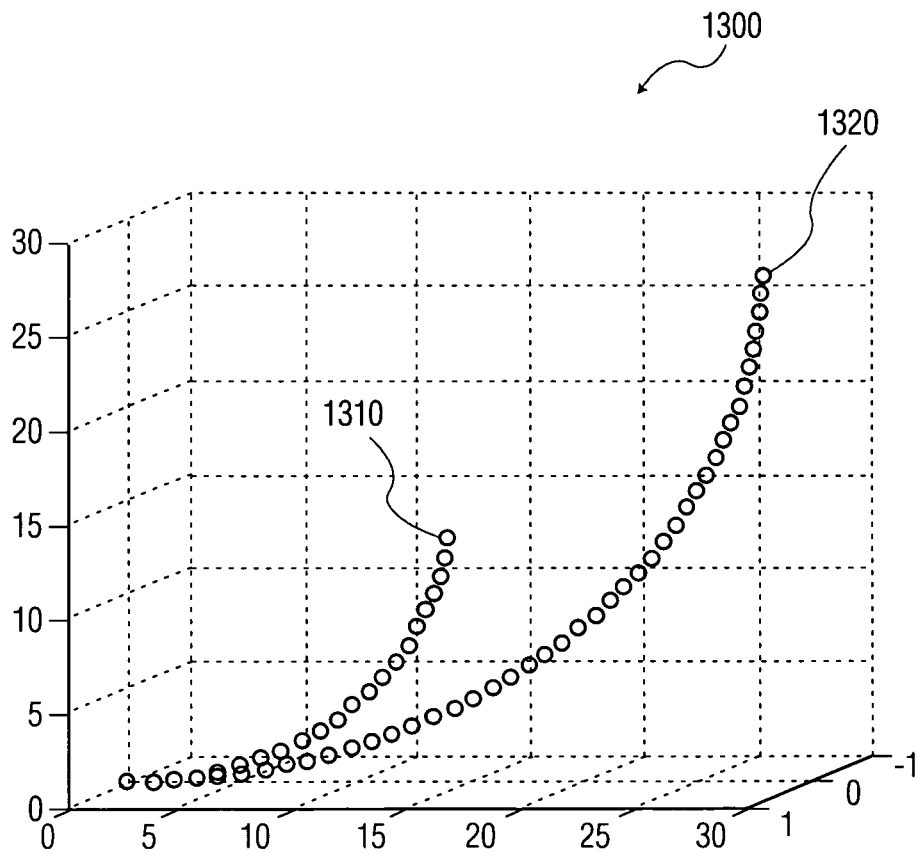
FIG. 13 illustrates a portion of a nominal neighborhood describing basic capabilities of a catheter.

Referring now to FIG. 13, part of the neighborhood is illustrated, showing the set of neighbors for arcs 1310 and 1320. These example arcs are for radii 14 mm and 28 mm, respectively. The notion of a thread denotes the precedence of visitable points. The arcs are about a 90 degree sweep into a circle having the turning radius specified. Ninety (90) degrees is the maximum required. The number of neighbors is therefore related to the size of the radius. That is, larger radii require more neighbors to cover the full 90 degree arc.

Figure 14:
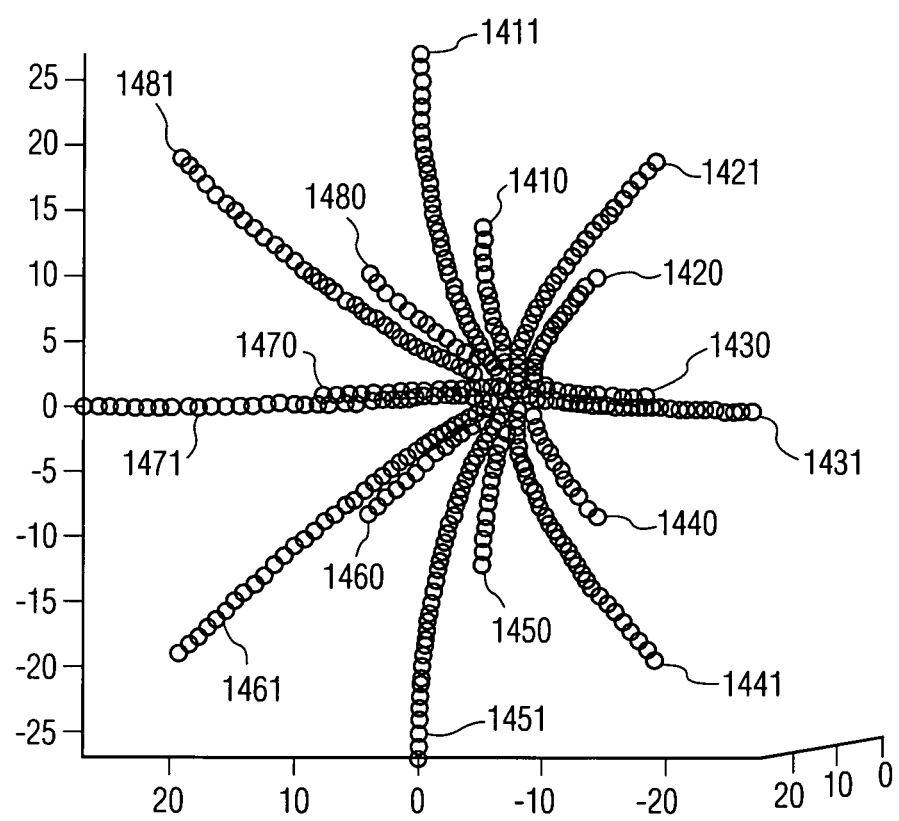
FIG. 14 illustrates a nominal neighborhood of nodes for a catheter comprising a change in locations and orientations of the tip of the catheter.

The set of arcs are then rotated about X for an arbitrary number of degrees, equally spaced. As in the case of the bronchoscope, the thread number implies a particular turning radius and rotation about X relative to the current orientation. FIG. 14 shows the completed nominal neighborhood having arc threads with radii of 14 mm and 28 mm.

Alternatively, more sophisticated models can be created to generate each of the threads of arbitrary shape. Clearly, the number of threads can be generated to an arbitrarily high number. The neighborhood could include many possible radii, to cover a greater volume of the 3D region. This neighborhood would be calculated in 3D as is shown by the analogous shape of FIG. 5, being similar to the group of threads in a thread/fiber optic lamp. So, every state in the volume is to be filled. An example of a complex metric might be one that further increases the cost by the percent of deviation from the center of the tube.

c.6 Constraints/Forbidden Regions/Obstacles

The input to this system is a segmented 3D image, such as from CT. This defines the free-space regions (i.e. where motion is permitted) and illegal regions of tissue. We can set the free-space nodes to 'uncosted', meaning that they are free to be updated. The illegal regions are set to 'infinity', a special (high) value which is also an indication that the path may not pass through.

c.7 'goal'/'start'

There are a few ways that the notions of 'start' and 'goal' can be used. In reality, the path can be calculated starting in either direction, taking care to calculate properly any directional costs. For example, driving backwards the wrong way along a one-way street is not permitted.

The 'goal' may be the 3D location targeted for angioplasty or RF ablation. This 'goal' is used as a 'seed' node for the search. The approach orientation may also be proposed by the doctor, such as if a biopsy is to be obtained from a tool fed through to the tip of the catheter. In this case, the 'start' node is not absolutely required.

The 'start' node may also be a 'seed' node, which is often located at the approximate center of the femoral artery for cardiac applications. In this case, the 'goal' node is not absolutely required.

C.8 Series of Events/Optimal Path

The same process is followed for the catheter as for the bronchoscope in terms of the core cost wave propagation, see B.8 discussion above.

C.9 Variations

If there is likely to be either control or sensory error, it is preferable to define the neighborhood more narrowly than theoretically possible. For example, the turning radius is enlarged beyond the smallest possible. This may compensate for unexpected control or sensing errors by a slight over correction during the procedure.

C.10 Path Following

After the search completes in FIG. 7, step 713, several processes can occur.

If a 'start' and 'goal' are identified, then the path can be rendered, or carried out by sending setpoint to the instrument, giving the advancement distance, and the alpha ($\alpha$) rotation of the catheter. This is the angle known from the thread number. Alternatively, the angle required can be determined either by calculating the optimal arc between the current position and orientation and the target position and orientation. In the preferred embodiment, for simulation, the thread number (such as from step 790 of FIG. 7) or curvature and angle are stored so that the settings are computed quickly.

If the 'start' node was the 'seed' node, then the 'goal' node may be 'picked' by the physician, by showing the reachable states in 3 space. The physician can then pick a target location, such as the location of a constricted vessel proposed for a stent. Alternatively, a Computer Aided Detection system can highlight suspected lesions, and the physician can more easily pick from this subset of points.

If the 'goal' node was the 'seed' node, then the catheter might be tracked in real-time. The x, y, z location of the tip of the catheter can be used to look up the matching location in the configuration space. Based on the location of the catheter's tip, the angle of the tip can be rotated to the proper angles.

The catheter has one control, the angle alpha ($\alpha$), plus the ability to advance into the patient. Advancement is performed by hand or can be performed with a machine. The path is followed from the 'start' to the 'goal', reading out each 'setpoint' in turn from the configuration space. The setpoints give the current location and orientation, the amount to advance to reach the next setpoint, and the thread number. The thread number gives the pose that the catheter should have in order to reach the next setpoint. In the example of FIG. 14, there are 16 threads that correspond to the following actions:

| Thread # | Change in Alpha in degrees |
| --- | --- |
| 1410 or 1411 | 0 |
| 1420 or 1421 | +45 |
| 1430 or 1431 | +90 |
| 1440 or 1441 | +135 |
| 1450 or 1451 | + or −180 |
| 1460 or 1461 | −135 |
| 1470 or 1471 | −90 |
| 1480 or 1481 | −45 |

Control Of A Beveled Needle (N)

Figure 15:
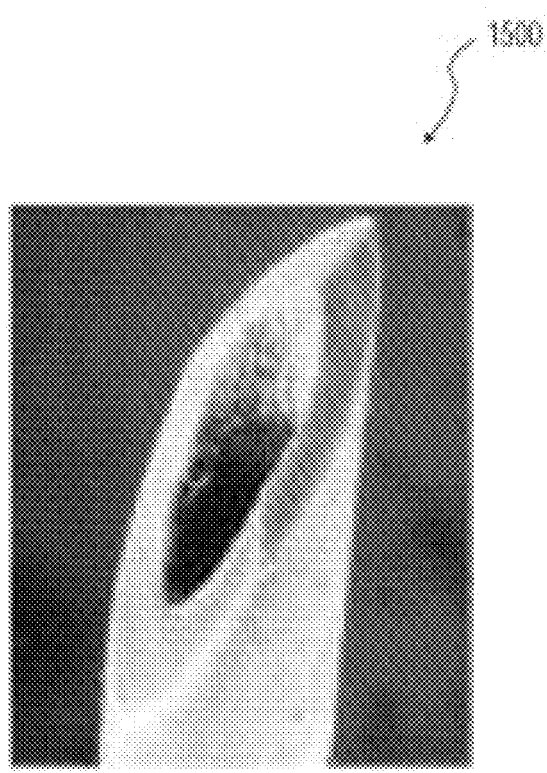
FIG. 15 illustrates a beveled needle.

A beveled needle, such as the one shown in FIG. 15, is known to strike a curved path (see, e.g., Robert J. Webster III, Noah J. Cowan, Gregory S. Chirikjian, and Allison M. Okamura, "Nonholonomic Modeling of Needle Steering", International Symposium of Experimental Robotics, Singapore, June, 2004 and [1] Robert J. Webster III, Jasenka Memisevic, and Allison M. Okamura, "Design Considerations for Robotic Needle Steering", IEEE International Conference on Robotics and Automation, Barcelona, April, 2005). The clinical objective is to use such needles to steer around obstacles and sensitive regions. In prior art methods, a plan for the beveled needle is restricted to 2 dimensions, requiring that the needle be turned at 0 degrees or 180 degrees to remain within a single plane. The system, apparatus and method of the present invention enables planning in 3 dimensions, including orientation, without requiring a 6 dimensional configuration space. In a preferred embodiment, the present invention is used with a single arc neighborhood representing the curvature created by inserting a beveled needle into a body. A target is selected, along with a preferred orientation of entry. The planner then uses the present invention to generate an optimal path from the entry area to the target ('goal'). There may be several equivalent 'optimal' paths reachable from the surface, if a heuristic is not used to drive and shorten the search. This can be valuable, since it gives the surgeon flexibility to choose a 'start' node during the procedure, given the external obstacles such as other equipment and assistants. The needle's interaction with different tissues can cause different types of curvature or even deflection (such as from a bone). Only with the ability to detect the type of tissue a-priori, as in the present invention, can the resulting curvatures be planned.

Pre-surgical Planning

Interventional guidance often requires pre-planning with CT or MRI images to determine the best access that generates the least damage while minimizing risk of catastrophic error. Pre-planning enables the surgeon to rehearse for possible problems, and incorporate tools to avoid them. It may be that a proposed tool cannot reach the 'goal' location without unreasonable cost, such as stress to the vessel wall. In this case, the present invention can be used to provide a cost for each of the various tools available, and identify the tool having the lowest cost for the given 'start' and 'goal'. This amounts to using the present invention to simulate the use of each tool in a given body.

Surgical Training

Since the system proposes a best path, including directives for control, it can also be used as feedback for practicing a surgery. In a preferred embodiment, this is accomplished by rendering the likely image at the tip of the tool. The image may be the orthogonal image to the scope or catheter, or may be an image surrounding the scope or catheter.

Surgical Control

Control commands for the tool can be directed to the doctor and an automated system that advances the tool and, for a scope, turns a scope's angle-setting dials according to the current configuration state.

Animal Examination

If quick and repeatable control is desired, such as in animal experiments, small scopes may be used and controlled for this application.

DNA-based Information

DNA information can be used to determine the best approach to sample a particular tumor or other lesion. This may be incorporated so that the desirable target selection, entry angles or cost weighting may be adapted based on the DNA indications. For example, blood vessels can have a higher weighting for some lesions where DNA shows a higher chance of cancer spread via vasculature. The resulting biopsy or excision path would then minimize paths that sever the lesion's supporting vasculature.

Apparatus and System

Figure 16:
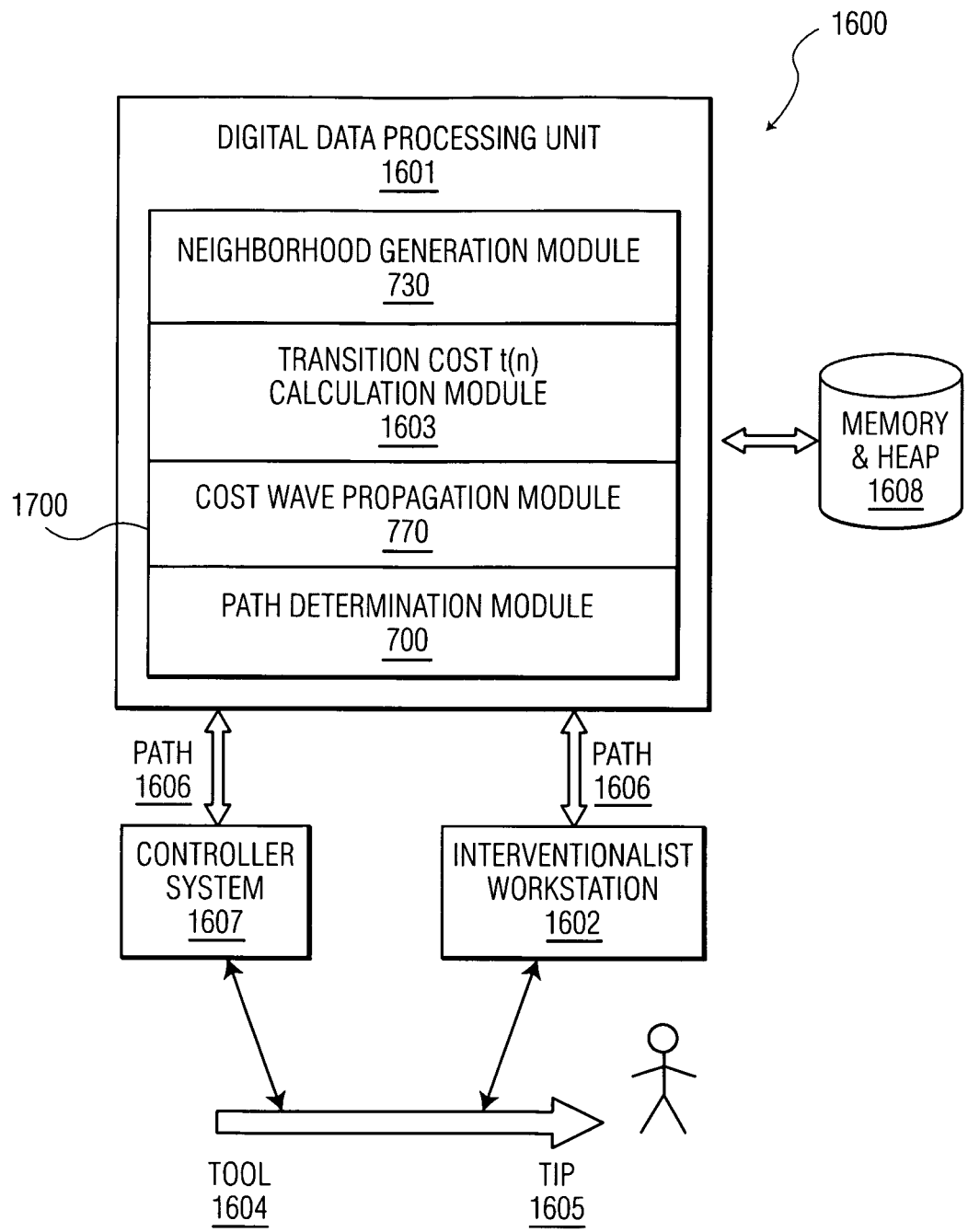
FIG. 16 illustrates a system for path planning according to the present invention.
Figure 17:
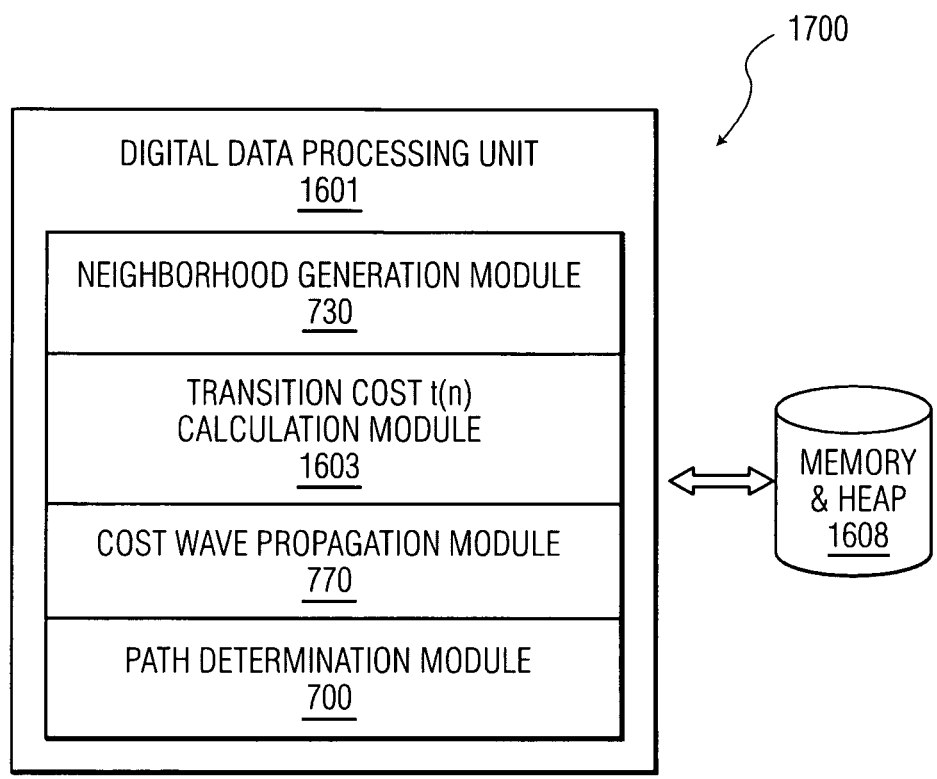
FIG. 17 illustrates an apparatus that performs path planning according to the present invention.

Referring now to FIG. 16, a system is illustrated for guiding a tool 1604 having a directable tip 1605. The system 1600 includes an apparatus 1700, illustrated in FIG. 17, for optimal path determination comprising a neighborhood generation module 730 to generate all reachable neighbors of a given pose, a transition cost t(n) calculation module 1603 to calculate the cost of transitioning to each neighbor from the given pose, a cost wave propagation module 770 to propagate cost waves from a goal to the given pose and a path determination module 700 that selects the lowest cost neighbor. An optimal path 1606 is determined based on cost (or some other objective function acting as a cost determinant) minimization, is stored by the digital data processing unit 1601 in the memory 1608, and is made available by the digital data processing unit 1601 either to an interventionalist 1602 or a tool controller system 1607. The optimal path and intermediate candidate poses are stored in memory 1608 and in a preferred embodiment a heap is used to order the candidate poses by cost, the minimum cost candidate being on top of the heap at any given time during path determination. The digital data processing unit 1601 directs the various modules of the apparatus 1700 in determination of an optimal path and stores intermediate and final paths in the memory and heap 1608 as well as provides determined optimal paths that have been stored previously in memory 1608 to controller systems 1607 and interventionalist workstations 1602, as directed.

While the preferred embodiments of the present invention have been illustrated and described, it will be understood by those skilled in the art that the system, apparatus and method as described herein are illustrative, and various changes and modifications may be made and equivalents may be substituted for elements thereof without departing from the true scope of the present invention. In addition, many modifications may be made to adapt the teachings of the present invention to catheter and scope path planning without departing from its central scope. Therefore, it is intended that the present invention not be limited to the particular embodiments disclosed as the best mode contemplated for carrying out the present invention, but that the present invention include all embodiments falling with the scope of the appended claims.

APPENDIX A

Straight Thread

| s | x | y | Theta | Phi | Cost |
|---|---|---|---|---|---|
| Alpha = 0 degrees | | | | | |
| Nominal arc in increments of 0.050 (2.865 degrees) | | | | | |
| 0.0 | 1.0 | 0.0 | 0.0 (0.0) | 0.0 (0.0) | 1.0 |
| 0.0 | 2.0 | 0.0 | 0.0 (0.0) | 0.0 (0.0) | 2.0 |
| 0.0 | 3.0 | 0.0 | 0.0 (0.0) | 0.0 (0.0) | 3.0 |
| 0.0 | 4.0 | 0.0 | 0.0 (0.0) | 0.0 (0.0) | 4.0 |
| 0.0 | 5.0 | 0.0 | 0.0 (0.0) | 0.0 (0.0) | 5.0 |
| 0.0 | 6.0 | 0.0 | 0.0 (0.0) | 0.0 (0.0) | 6.0 |
| 0.0 | 7.0 | 0.0 | 0.0 (0.0) | 0.0 (0.0) | 7.0 |
| 0.0 | 8.0 | 0.0 | 0.0 (0.0) | 0.0 (0.0) | 8.0 |
| 0.0 | 9.0 | 0.0 | 0.0 (0.0) | 0.0 (0.0) | 9.0 |
| 0.0 | 10.0 | 0.0 | 0.0 (0.0) | 0.0 (0.0) | 10.0 |
| 0.0 | 11.0 | 0.0 | 0.0 (0.0) | 0.0 (0.0) | 11.0 |
| 0.0 | 12.0 | 0.0 | 0.0 (0.0) | 0.0 (0.0) | 12.0 |
| 0.0 | 13.0 | 0.0 | 0.0 (0.0) | 0.0 (0.0) | 13.0 |
| 0.0 | 14.0 | 0.0 | 0.0 (0.0) | 0.0 (0.0) | 14.0 |
| 0.0 | 15.0 | 0.0 | 0.0 (0.0) | 0.0 (0.0) | 15.0 |
| 0.0 | 16.0 | 0.0 | 0.0 (0.0) | 0.0 (0.0) | 16.0 |
| 0.0 | 17.0 | 0.0 | 0.0 (0.0) | 0.0 (0.0) | 17.0 |
| 0.0 | 18.0 | 0.0 | 0.0 (0.0) | 0.0 (0.0) | 18.0 |
| 0.0 | 19.0 | 0.0 | 0.0 (0.0) | 0.0 (0.0) | 19.0 |
| 0.0 | 20.0 | 0.0 | 0.0 (0.0) | 0.0 (0.0) | 20.0 |
| 0.0 | 21.0 | 0.0 | 0.0 (0.0) | 0.0 (0.0) | 21.0 |
| 0.0 | 22.0 | 0.0 | 0.0 (0.0) | 0.0 (0.0) | 22.0 |
| 0.0 | 23.0 | 0.0 | 0.0 (0.0) | 0.0 (0.0) | 23.0 |
| 0.0 | 24.0 | 0.0 | 0.0 (0.0) | 0.0 (0.0) | 24.0 |
| 0.0 | 25.0 | 0.0 | 0.0 (0.0) | 0.0 (0.0) | 25.0 |
| 0.0 | 26.0 | 0.0 | 0.0 (0.0) | 0.0 (0.0) | 26.0 |
| 0.0 | 27.0 | 0.0 | 0.0 (0.0) | 0.0 (0.0) | 27.0 |
| 0.0 | 28.0 | 0.0 | 0.0 (0.0) | 0.0 (0.0) | 28.0 |
| 0.0 | 29.0 | 0.0 | 0.0 (0.0) | 0.0 (0.0) | 29.0 |
| 0.0 | 30.0 | 0.0 | 0.0 (0.0) | 0.0 (0.0) | 30.0 |
| 0.0 | 31.0 | 0.0 | 0.0 (0.0) | 0.0 (0.0) | 31.0 |
| 0.0 | 32.0 | 0.0 | 0.0 (0.0) | 0.0 (0.0) | 32.0 |
| 0.0 | 33.0 | 0.0 | 0.0 (0.0) | 0.0 (0.0) | 33.0 |
| 0.0 | 34.0 | 0.0 | 0.0 (0.0) | 0.0 (0.0) | 34.0 |
| 0.0 | 35.0 | 0.0 | 0.0 (0.0) | 0.0 (0.0) | 35.0 |
| 0.0 | 36.0 | 0.0 | 0.0 (0.0) | 0.0 (0.0) | 36.0 |
| 0.0 | 37.0 | 0.0 | 0.0 (0.0) | 0.0 (0.0) | 37.0 |
| 0.0 | 38.0 | 0.0 | 0.0 (0.0) | 0.0 (0.0) | 38.0 |
| 0.0 | 39.0 | 0.0 | 0.0 (0.0) | 0.0 (0.0) | 39.0 |
| 0.0 | 40.0 | 0.0 | 0.0 (0.0) | 0.0 (0.0) | 40.0 |
| Alpha Rotation of this thread = 0.0 (0.0) | | | | | |
| 0.0 | 1.0 | 0.0 | 0.0 (0.0) | 0.1 (2.9) | 1.0 |
| 0.0 | 2.0 | 0.1 | 0.0 (0.0) | 0.1 (5.7) | 2.0 |
| 0.0 | 3.0 | 0.2 | 0.0 (0.0) | 0.2 (8.6) | 3.0 |
| 0.0 | 4.0 | 0.4 | 0.0 (0.0) | 0.2 (11.5) | 4.0 |
| 0.0 | 4.9 | 0.6 | 0.0 (0.0) | 0.3 (14.3) | 5.0 |
| 0.0 | 5.9 | 0.9 | 0.0 (0.0) | 0.3 (17.2) | 6.0 |
| 0.0 | 6.9 | 1.2 | 0.0 (0.0) | 0.3 (20.1) | 7.0 |
| 0.0 | 7.8 | 1.6 | 0.0 (0.0) | 0.4 (22.9) | 8.0 |
| 0.0 | 8.7 | 2.0 | 0.0 (0.0) | 0.4 (25.8) | 9.0 |
| 0.0 | 9.6 | 2.4 | 0.0 (0.0) | 0.5 (28.6) | 10.0 |
| 0.0 | 10.5 | 2.9 | 0.0 (0.0) | 0.6 (31.5) | 11.0 |
| 0.0 | 11.3 | 3.5 | 0.0 (0.0) | 0.6 (34.4) | 12.0 |
| 0.0 | 12.1 | 4.1 | 0.0 (0.0) | 0.6 (37.2) | 13.0 |
| 0.0 | 12.9 | 4.7 | 0.0 (0.0) | 0.7 (40.1) | 14.0 |
| 0.0 | 13.6 | 5.4 | 0.0 (0.0) | 0.8 (43.0) | 15.0 |
| 0.0 | 14.3 | 6.1 | 0.0 (0.0) | 0.8 (45.8) | 16.0 |
| 0.0 | 15.0 | 6.8 | 0.0 (0.0) | 0.9 (48.7) | 17.0 |
| 0.0 | 15.7 | 7.6 | 0.0 (0.0) | 0.9 (51.6) | 18.0 |
| 0.0 | 16.3 | 8.4 | 0.0 (0.0) | 0.9 (54.4) | 19.0 |
| 0.0 | 16.8 | 9.2 | 0.0 (0.0) | 1.0 (57.3) | 20.0 |
| 0.0 | 17.3 | 10.0 | 0.0 (0.0) | 1.0 (60.2) | 21.0 |
| 0.0 | 17.8 | 10.9 | 0.0 (0.0) | 1.1 (63.0) | 22.0 |
| 0.0 | 18.3 | 11.8 | 0.0 (0.0) | 1.1 (65.9) | 23.0 |
| 0.0 | 18.6 | 12.8 | 0.0 (0.0) | 1.2 (68.8) | 24.0 |
| 0.0 | 19.0 | 13.7 | 0.0 (0.0) | 1.3 (71.6) | 25.0 |
| 0.0 | 19.3 | 14.7 | 0.0 (0.0) | 1.3 (74.5) | 26.0 |
| 0.0 | 19.5 | 15.6 | 0.0 (0.0) | 1.4 (77.3) | 27.0 |
| 0.0 | 19.7 | 16.6 | 0.0 (0.0) | 1.4 (80.2) | 28.0 |
| 0.0 | 19.9 | 17.6 | 0.0 (0.0) | 1.5 (83.1) | 29.0 |
| 0.0 | 19.9 | 18.6 | 0.0 (0.0) | 1.5 (85.9) | 30.0 |
| 0.0 | 20.0 | 19.6 | 0.0 (0.0) | 1.5 (88.8) | 31.0 |
| Alpha Rotation of this thread = 0.8 (45.0) | | | | | |
| 0.0 | 1.0 | 0.0 | 0.0 (2.0) | 0.0 (2.0) | 1.0 |
| 0.1 | 2.0 | 0.1 | 0.1 (4.1) | 0.1 (4.1) | 2.0 |
| 0.2 | 3.0 | 0.2 | 0.1 (6.1) | 0.1 (6.1) | 3.0 |
| 0.3 | 4.0 | 0.3 | 0.1 (8.1) | 0.1 (8.1) | 4.0 |
| 0.4 | 4.9 | 0.4 | 0.2 (10.1) | 0.2 (10.1) | 5.0 |
| 0.6 | 5.9 | 0.6 | 0.2 (12.2) | 0.2 (12.2) | 6.0 |
| 0.9 | 6.9 | 0.9 | 0.2 (14.2) | 0.2 (14.2) | 7.0 |
| 1.1 | 7.8 | 1.1 | 0.3 (16.2) | 0.3 (16.2) | 8.0 |
| 1.4 | 8.7 | 1.4 | 0.3 (18.2) | 0.3 (18.2) | 9.0 |
| 1.7 | 9.6 | 1.7 | 0.4 (20.3) | 0.4 (20.3) | 10.0 |
| 2.1 | 10.5 | 2.1 | 0.4 (22.3) | 0.4 (22.3) | 11.0 |
| 2.5 | 11.3 | 2.5 | 0.4 (24.3) | 0.4 (24.3) | 12.0 |
| 2.9 | 12.1 | 2.9 | 0.5 (26.3) | 0.5 (26.3) | 13.0 |
| 3.3 | 12.9 | 3.3 | 0.5 (28.4) | 0.5 (28.4) | 14.0 |

APPENDIX A-continued

Straight Thread

| s | x | y | Theta | Phi | Cost |
|---|---|---|-------|-----|------|
| 3.8 | 13.6 | 3.8 | 0.5 (30.4) | 0.5 (30.4) | 15.0 |
| 4.3 | 14.3 | 4.3 | 0.6 (32.4) | 0.6 (32.4) | 16.0 |
| 4.8 | 15.0 | 4.8 | 0.6 (34.4) | 0.6 (34.4) | 17.0 |
| 5.4 | 15.7 | 5.4 | 0.6 (36.5) | 0.6 (36.5) | 18.0 |
| 5.9 | 16.3 | 5.9 | 0.7 (38.5) | 0.7 (38.5) | 19.0 |
| 6.5 | 16.8 | 6.5 | 0.7 (40.5) | 0.7 (40.5) | 20.0 |
| 7.1 | 17.3 | 7.1 | 0.7 (42.5) | 0.7 (42.5) | 21.0 |
| 7.7 | 17.8 | 7.7 | 0.8 (44.6) | 0.8 (44.6) | 22.0 |
| 8.4 | 18.3 | 8.4 | 0.8 (46.6) | 0.8 (46.6) | 23.0 |
| 9.0 | 18.6 | 9.0 | 0.8 (48.6) | 0.8 (48.6) | 24.0 |
| 9.7 | 19.0 | 9.7 | 0.9 (50.6) | 0.9 (50.6) | 25.0 |
| 10.4 | 19.3 | 10.4 | 0.9 (52.7) | 0.9 (52.7) | 26.0 |
| 11.0 | 19.5 | 11.0 | 1.0 (54.7) | 1.0 (54.7) | 27.0 |
| 11.7 | 19.7 | 11.7 | 1.0 (56.7) | 1.0 (56.7) | 28.0 |
| 12.4 | 19.9 | 12.4 | 1.0 (58.7) | 1.0 (58.7) | 29.0 |
| 13.1 | 19.9 | 13.1 | 1.1 (60.8) | 1.1 (60.8) | 30.0 |
| 13.8 | 20.0 | 13.8 | 1.1 (62.8) | 1.1 (62.8) | 31.0 |
| Alpha Rotation of this thread = 1.6 (90.0) | | | | | |
| 0.0 | 1.0 | -0.0 | 0.1 (2.9) | -0.0 (-0.0) | 1.0 |
| 0.1 | 2.0 | -0.0 | 0.1 (5.7) | -0.0 (-0.0) | 2.0 |
| 0.2 | 3.0 | -0.0 | 0.2 (8.6) | -0.0 (-0.0) | 3.0 |
| 0.4 | 4.0 | -0.0 | 0.2 (11.5) | -0.0 (-0.0) | 4.0 |
| 0.6 | 4.9 | -0.0 | 0.3 (14.3) | -0.0 (-0.0) | 5.0 |
| 0.9 | 5.9 | -0.0 | 0.3 (17.2) | -0.0 (-0.0) | 6.0 |
| 1.2 | 6.9 | -0.0 | 0.3 (20.1) | -0.0 (-0.0) | 7.0 |
| 1.6 | 7.8 | -0.0 | 0.4 (22.9) | -0.0 (-0.0) | 8.0 |
| 2.0 | 8.7 | -0.0 | 0.4 (25.8) | -0.0 (-0.0) | 9.0 |
| 2.4 | 9.6 | -0.0 | 0.5 (28.6) | -0.0 (-0.0) | 10.0 |
| 2.9 | 10.5 | -0.0 | 0.6 (31.5) | -0.0 (-0.0) | 11.0 |
| 3.5 | 11.3 | -0.0 | 0.6 (34.4) | -0.0 (-0.0) | 12.0 |
| 4.1 | 12.1 | -0.0 | 0.6 (37.2) | -0.0 (-0.0) | 13.0 |
| 4.7 | 12.9 | -0.0 | 0.7 (40.1) | -0.0 (-0.0) | 14.0 |
| 5.4 | 13.6 | -0.0 | 0.8 (43.0) | -0.0 (-0.0) | 15.0 |
| 6.1 | 14.3 | -0.0 | 0.8 (45.8) | -0.0 (-0.0) | 16.0 |
| 6.8 | 15.0 | -0.0 | 0.9 (48.7) | -0.0 (-0.0) | 17.0 |
| 7.6 | 15.7 | -0.0 | 0.9 (51.6) | -0.0 (-0.0) | 18.0 |
| 8.4 | 16.3 | -0.0 | 0.9 (54.4) | -0.0 (-0.0) | 19.0 |
| 9.2 | 16.8 | -0.0 | 1.0 (57.3) | -0.0 (-0.0) | 20.0 |
| 10.0 | 17.3 | -0.0 | 1.0 (60.2) | -0.0 (-0.0) | 21.0 |
| 10.9 | 17.8 | -0.0 | 1.1 (63.0) | -0.0 (-0.0) | 22.0 |
| 11.8 | 18.3 | -0.0 | 1.1 (65.9) | -0.0 (-0.0) | 23.0 |
| 12.8 | 18.6 | -0.0 | 1.2 (68.8) | -0.0 (-0.0) | 24.0 |
| 13.7 | 19.0 | -0.0 | 1.3 (71.6) | -0.0 (-0.0) | 25.0 |
| 14.7 | 19.3 | -0.0 | 1.3 (74.5) | -0.0 (-0.0) | 26.0 |
| 15.6 | 19.5 | -0.0 | 1.4 (77.3) | -0.0 (-0.0) | 27.0 |
| 16.6 | 19.7 | -0.0 | 1.4 (80.2) | -0.0 (-0.0) | 28.0 |
| 17.6 | 19.9 | -0.0 | 1.5 (83.1) | -0.0 (-0.0) | 29.0 |
| 18.6 | 19.9 | -0.0 | 1.5 (85.9) | -0.0 (-0.0) | 30.0 |
| 19.6 | 20.0 | -0.0 | 1.5 (88.8) | -0.0 (-0.0) | 31.0 |
| Alpha Rotation of this thread = 2.4 (135.0) | | | | | |
| 0.0 | 1.0 | -0.0 | 0.0 (2.0) | -0.0 (-2.0) | 1.0 |
| 0.1 | 2.0 | -0.1 | 0.1 (4.1) | -0.1 (-4.1) | 2.0 |
| 0.2 | 3.0 | -0.2 | 0.1 (6.1) | -0.1 (-6.1) | 3.0 |
| 0.3 | 4.0 | -0.3 | 0.1 (8.1) | -0.1 (-8.1) | 4.0 |
| 0.4 | 4.9 | -0.4 | 0.2 (10.1) | -0.2 (-10.1) | 5.0 |
| 0.6 | 5.9 | -0.6 | 0.2 (12.2) | -0.2 (-12.2) | 6.0 |
| 0.9 | 6.9 | -0.9 | 0.2 (14.2) | -0.2 (-14.2) | 7.0 |
| 1.1 | 7.8 | -1.1 | 0.3 (16.2) | -0.3 (-16.2) | 8.0 |
| 1.4 | 8.7 | -1.4 | 0.3 (18.2) | -0.3 (-18.2) | 9.0 |
| 1.7 | 9.6 | -1.7 | 0.4 (20.3) | -0.4 (-20.3) | 10.0 |
| 2.1 | 10.5 | -2.1 | 0.4 (22.3) | -0.4 (-22.3) | 11.0 |
| 2.5 | 11.3 | -2.5 | 0.4 (24.3) | -0.4 (-24.3) | 12.0 |
| 2.9 | 12.1 | -2.9 | 0.5 (26.3) | -0.5 (-26.3) | 13.0 |
| 3.3 | 12.9 | -3.3 | 0.5 (28.4) | -0.5 (-28.4) | 14.0 |
| 3.8 | 13.6 | -3.8 | 0.5 (30.4) | -0.5 (-30.4) | 15.0 |
| 4.3 | 14.3 | -4.3 | 0.6 (32.4) | -0.6 (-32.4) | 16.0 |
| 4.8 | 15.0 | -4.8 | 0.6 (34.4) | -0.6 (-34.4) | 17.0 |
| 5.4 | 15.7 | -5.4 | 0.6 (36.5) | -0.6 (-36.5) | 18.0 |
| 5.9 | 16.3 | -5.9 | 0.7 (38.5) | -0.7 (-38.5) | 19.0 |
| 6.5 | 16.8 | -6.5 | 0.7 (40.5) | -0.7 (-40.5) | 20.0 |
| 7.1 | 17.3 | -7.1 | 0.7 (42.5) | -0.7 (-42.5) | 21.0 |
| 7.7 | 17.8 | -7.7 | 0.8 (44.6) | -0.8 (-44.6) | 22.0 |
| 8.4 | 18.3 | -8.4 | 0.8 (46.6) | -0.8 (-46.6) | 23.0 |
| 9.0 | 18.6 | -9.0 | 0.8 (48.6) | -0.8 (-48.6) | 24.0 |
| 9.7 | 19.0 | -9.7 | 0.9 (50.6) | -0.9 (-50.6) | 25.0 |
| 10.4 | 19.3 | -10.4 | 0.9 (52.7) | -0.9 (-52.7) | 26.0 |
| 11.0 | 19.5 | -11.0 | 1.0 (54.7) | -1.0 (-54.7) | 27.0 |
| 11.7 | 19.7 | -11.7 | 1.0 (56.7) | -1.0 (-56.7) | 28.0 |
| 12.4 | 19.9 | -12.4 | 1.0 (58.7) | -1.0 (-58.7) | 29.0 |
| 13.1 | 19.9 | -13.1 | 1.1 (60.8) | -1.1 (-60.8) | 30.0 |
| 13.8 | 20.0 | -13.8 | 1.1 (62.8) | -1.1 (-62.8) | 31.0 |
| Alpha Rotation of this thread = 3.1 (180.0) | | | | | |
| -0.0 | 1.0 | -0.0 | -0.0 (-0.0) | -0.1 (-2.9) | 1.0 |
| -0.0 | 2.0 | -0.1 | -0.0 (-0.0) | -0.1 (-5.7) | 2.0 |
| -0.0 | 3.0 | -0.2 | -0.0 (-0.0) | -0.2 (-8.6) | 3.0 |
| -0.0 | 4.0 | -0.4 | -0.0 (-0.0) | -0.2 (-11.5) | 4.0 |
| -0.0 | 4.9 | -0.6 | -0.0 (-0.0) | -0.3 (-14.3) | 5.0 |
| -0.0 | 5.9 | -0.9 | -0.0 (-0.0) | -0.3 (-17.2) | 6.0 |
| -0.0 | 6.9 | -1.2 | -0.0 (-0.0) | -0.3 (-20.1) | 7.0 |
| -0.0 | 7.8 | -1.6 | -0.0 (-0.0) | -0.4 (-22.9) | 8.0 |
| -0.0 | 8.7 | -2.0 | -0.0 (-0.0) | -0.4 (-25.8) | 9.0 |
| -0.0 | 9.6 | -2.4 | -0.0 (-0.0) | -0.5 (-28.6) | 10.0 |
| -0.0 | 10.5 | -2.9 | -0.0 (-0.0) | -0.6 (-31.5) | 11.0 |
| -0.0 | 11.3 | -3.5 | -0.0 (-0.0) | -0.6 (-34.4) | 12.0 |
| -0.0 | 12.1 | -4.1 | -0.0 (-0.0) | -0.6 (-37.2) | 13.0 |
| -0.0 | 12.9 | -4.7 | -0.0 (-0.0) | -0.7 (-40.1) | 14.0 |
| -0.0 | 13.6 | -5.4 | -0.0 (-0.0) | -0.8 (-43.0) | 15.0 |
| -0.0 | 14.3 | -6.1 | -0.0 (-0.0) | -0.8 (-45.8) | 16.0 |
| -0.0 | 15.0 | -6.8 | -0.0 (-0.0) | -0.9 (-48.7) | 17.0 |
| -0.0 | 15.7 | -7.6 | -0.0 (-0.0) | -0.9 (-51.6) | 18.0 |
| -0.0 | 16.3 | -8.4 | -0.0 (-0.0) | -0.9 (-54.4) | 19.0 |
| -0.0 | 16.8 | -9.2 | -0.0 (-0.0) | -1.0 (-57.3) | 20.0 |
| -0.0 | 17.3 | -10.0 | -0.0 (-0.0) | -1.0 (-60.2) | 21.0 |
| -0.0 | 17.8 | -10.9 | -0.0 (-0.0) | -1.1 (-63.0) | 22.0 |
| -0.0 | 18.3 | -11.8 | -0.0 (-0.0) | -1.1 (-65.9) | 23.0 |
| -0.0 | 18.6 | -12.8 | -0.0 (-0.0) | -1.2 (-68.8) | 24.0 |
| -0.0 | 19.0 | -13.7 | -0.0 (-0.0) | -1.3 (-71.6) | 25.0 |
| -0.0 | 19.3 | -14.7 | -0.0 (-0.0) | -1.3 (-74.5) | 26.0 |
| -0.0 | 19.5 | -15.6 | -0.0 (-0.0) | -1.4 (-77.3) | 27.0 |
| -0.0 | 19.7 | -16.6 | -0.0 (-0.0) | -1.4 (-80.2) | 28.0 |
| -0.0 | 19.9 | -17.6 | -0.0 (-0.0) | -1.5 (-83.1) | 29.0 |
| -0.0 | 19.9 | -18.6 | -0.0 (-0.0) | -1.5 (-85.9) | 30.0 |
| -0.0 | 20.0 | -19.6 | -0.0 (-0.0) | -1.5 (-88.8) | 31.0 |
| Alpha Rotation of this thread = 3.9 (225.0) | | | | | |
| -0.0 | 1.0 | -0.0 | -0.0 (-2.0) | -0.0 (-2.0) | 1.0 |
| -0.1 | 2.0 | -0.1 | -0.1 (-4.1) | -0.1 (-4.1) | 2.0 |
| -0.2 | 3.0 | -0.2 | -0.1 (-6.1) | -0.1 (-6.1) | 3.0 |
| -0.3 | 4.0 | -0.3 | -0.1 (-8.1) | -0.1 (-8.1) | 4.0 |
| -0.4 | 4.9 | -0.4 | -0.2 (-10.1) | -0.2 (-10.1) | 5.0 |
| -0.6 | 5.9 | -0.6 | -0.2 (-12.2) | -0.2 (-12.2) | 6.0 |
| -0.9 | 6.9 | -0.9 | -0.2 (-14.2) | -0.2 (-14.2) | 7.0 |
| -1.1 | 7.8 | -1.1 | -0.3 (-16.2) | -0.3 (-16.2) | 8.0 |
| -1.4 | 8.7 | -1.4 | -0.3 (-18.2) | -0.3 (-18.2) | 9.0 |
| -1.7 | 9.6 | -1.7 | -0.4 (-20.3) | -0.4 (-20.3) | 10.0 |
| -2.1 | 10.5 | -2.1 | -0.4 (-22.3) | -0.4 (-22.3) | 11.0 |
| -2.5 | 11.3 | -2.5 | -0.4 (-24.3) | -0.4 (-24.3) | 12.0 |
| -2.9 | 12.1 | -2.9 | -0.5 (-26.3) | -0.5 (-26.3) | 13.0 |
| -3.3 | 12.9 | -3.3 | -0.5 (-28.4) | -0.5 (-28.4) | 14.0 |
| -3.8 | 13.6 | -3.8 | -0.5 (-30.4) | -0.5 (-30.4) | 15.0 |
| -4.3 | 14.3 | -4.3 | -0.6 (-32.4) | -0.6 (-32.4) | 16.0 |
| -4.8 | 15.0 | -4.8 | -0.6 (-34.4) | -0.6 (-34.4) | 17.0 |
| -5.4 | 15.7 | -5.4 | -0.6 (-36.5) | -0.6 (-36.5) | 18.0 |
| -5.9 | 16.3 | -5.9 | -0.7 (-38.5) | -0.7 (-38.5) | 19.0 |
| -6.5 | 16.8 | -6.5 | -0.7 (-40.5) | -0.7 (-40.5) | 20.0 |
| -7.1 | 17.3 | -7.1 | -0.7 (-42.5) | -0.7 (-42.5) | 21.0 |
| -7.7 | 17.8 | -7.7 | -0.8 (-44.6) | -0.8 (-44.6) | 22.0 |
| -8.4 | 18.3 | -8.4 | -0.8 (-46.6) | -0.8 (-46.6) | 23.0 |
| -9.0 | 18.6 | -9.0 | -0.8 (-48.6) | -0.8 (-48.6) | 24.0 |
| -9.7 | 19.0 | -9.7 | -0.9 (-50.6) | -0.9 (-50.6) | 25.0 |
| -10.4 | 19.3 | -10.4 | -0.9 (-52.7) | -0.9 (-52.7) | 26.0 |
| -11.0 | 19.5 | -11.0 | -1.0 (-54.7) | -1.0 (-54.7) | 27.0 |
| -11.7 | 19.7 | -11.7 | -1.0 (-56.7) | -1.0 (-56.7) | 28.0 |
| -12.4 | 19.9 | -12.4 | -1.0 (-58.7) | -1.0 (-58.7) | 29.0 |

APPENDIX A-continued

Straight Thread

| s | x | y | Theta | Phi | Cost |
|---|---|---|-------|-----|------|
| −13.1 | 19.9 | −13.1 | −1.1 (−60.8) | −1.1 (−60.8) | 30.0 |
| −13.8 | 20.0 | −13.8 | −1.1 (−62.8) | −1.1 (−62.8) | 31.0 |
| Alpha Rotation of this thread = 4.7 (270.0) | | | | | |
| −0.0 | 1.0 | 0.0 | −0.1 (−2.9) | 0.0 (0.0) | 1.0 |
| −0.1 | 2.0 | 0.0 | −0.1 (−5.7) | 0.0 (0.0) | 2.0 |
| −0.2 | 3.0 | 0.0 | −0.2 (−8.6) | 0.0 (0.0) | 3.0 |
| −0.4 | 4.0 | 0.0 | −0.2 (−11.5) | 0.0 (0.0) | 4.0 |
| −0.6 | 4.9 | 0.0 | −0.3 (−14.3) | 0.0 (0.0) | 5.0 |
| −0.9 | 5.9 | 0.0 | −0.3 (−17.2) | 0.0 (0.0) | 6.0 |
| −1.2 | 6.9 | 0.0 | −0.3 (−20.1) | 0.0 (0.0) | 7.0 |
| −1.6 | 7.8 | 0.0 | −0.4 (−22.9) | 0.0 (0.0) | 8.0 |
| −2.0 | 8.7 | 0.0 | −0.4 (−25.8) | 0.0 (0.0) | 9.0 |
| −2.4 | 9.6 | 0.0 | −0.5 (−28.6) | 0.0 (0.0) | 10.0 |
| −2.9 | 10.5 | 0.0 | −0.6 (−31.5) | 0.0 (0.0) | 11.0 |
| −3.5 | 11.3 | 0.0 | −0.6 (−34.4) | 0.0 (0.0) | 12.0 |
| −4.1 | 12.1 | 0.0 | −0.6 (−37.2) | 0.0 (0.0) | 13.0 |
| −4.7 | 12.9 | 0.0 | −0.7 (−40.1) | 0.0 (0.0) | 14.0 |
| −5.4 | 13.6 | 0.0 | −0.8 (−43.0) | 0.0 (0.0) | 15.0 |
| −6.1 | 14.3 | 0.0 | −0.8 (−45.8) | 0.0 (0.0) | 16.0 |
| −6.8 | 15.0 | 0.0 | −0.9 (−48.7) | 0.0 (0.0) | 17.0 |
| −7.6 | 15.7 | 0.0 | −0.9 (−51.6) | 0.0 (0.0) | 18.0 |
| −8.4 | 16.3 | 0.0 | −0.9 (−54.4) | 0.0 (0.0) | 19.0 |
| −9.2 | 16.8 | 0.0 | −1.0 (−57.3) | 0.0 (0.0) | 20.0 |
| −10.0 | 17.3 | 0.0 | −1.0 (−60.2) | 0.0 (0.0) | 21.0 |
| −10.9 | 17.8 | 0.0 | −1.1 (−63.0) | 0.0 (0.0) | 22.0 |
| −11.8 | 18.3 | 0.0 | −1.1 (−65.9) | 0.0 (0.0) | 23.0 |
| −12.8 | 18.6 | 0.0 | −1.2 (−68.8) | 0.0 (0.0) | 24.0 |
| −13.7 | 19.0 | 0.0 | −1.3 (−71.6) | 0.0 (0.0) | 25.0 |
| −14.7 | 19.3 | 0.0 | −1.3 (−74.5) | 0.0 (0.0) | 26.0 |
| −15.6 | 19.5 | 0.0 | −1.4 (−77.3) | 0.0 (0.0) | 27.0 |
| −16.6 | 19.7 | 0.0 | −1.4 (−80.2) | 0.0 (0.0) | 28.0 |
| −17.6 | 19.9 | 0.0 | −1.5 (−83.1) | 0.0 (0.0) | 29.0 |
| −18.6 | 19.9 | 0.0 | −1.5 (−85.9) | 0.0 (0.0) | 30.0 |
| −19.6 | 20.0 | 0.0 | −1.5 (−88.8) | 0.0 (0.0) | 31.0 |
| Alpha Rotation of this thread = 5.5 (315.0) | | | | | |
| −0.0 | 1.0 | 0.0 | −0.0 (−2.0) | 0.0 (2.0) | 1.0 |
| −0.1 | 2.0 | 0.1 | −0.1 (−4.1) | 0.1 (4.1) | 2.0 |
| −0.2 | 3.0 | 0.2 | −0.1 (−6.1) | 0.1 (6.1) | 3.0 |
| −0.3 | 4.0 | 0.3 | −0.1 (−8.1) | 0.1 (8.1) | 4.0 |
| −0.4 | 4.9 | 0.4 | −0.2 (−10.1) | 0.2 (10.1) | 5.0 |
| −0.6 | 5.9 | 0.6 | −0.2 (−12.2) | 0.2 (12.2) | 6.0 |
| −0.9 | 6.9 | 0.9 | −0.2 (−14.2) | 0.2 (14.2) | 7.0 |
| −1.1 | 7.8 | 1.1 | −0.3 (−16.2) | 0.3 (16.2) | 8.0 |
| −1.4 | 8.7 | 1.4 | −0.3 (−18.2) | 0.3 (18.2) | 9.0 |
| −1.7 | 9.6 | 1.7 | −0.4 (−20.3) | 0.4 (20.3) | 10.0 |
| −2.1 | 10.5 | 2.1 | −0.4 (−22.3) | 0.4 (22.3) | 11.0 |
| −2.5 | 11.3 | 2.5 | −0.4 (−24.3) | 0.4 (24.3) | 12.0 |
| −2.9 | 12.1 | 2.9 | −0.5 (−26.3) | 0.5 (26.3) | 13.0 |
| −3.3 | 12.9 | 3.3 | −0.5 (−28.4) | 0.5 (28.4) | 14.0 |
| −3.8 | 13.6 | 3.8 | −0.5 (−30.4) | 0.5 (30.4) | 15.0 |
| −4.3 | 14.3 | 4.3 | −0.6 (−32.4) | 0.6 (32.4) | 16.0 |
| −4.8 | 15.0 | 4.8 | −0.6 (−34.4) | 0.6 (34.4) | 17.0 |
| −5.4 | 15.7 | 5.4 | −0.6 (−36.5) | 0.6 (36.5) | 18.0 |
| −5.9 | 16.3 | 5.9 | −0.7 (−38.5) | 0.7 (38.5) | 19.0 |
| −6.5 | 16.8 | 6.5 | −0.7 (−40.5) | 0.7 (40.5) | 20.0 |
| −7.1 | 17.3 | 7.1 | −0.7 (−42.5) | 0.7 (42.5) | 21.0 |
| −7.7 | 17.8 | 7.7 | −0.8 (−44.6) | 0.8 (44.6) | 22.0 |
| −8.4 | 18.3 | 8.4 | −0.8 (−46.6) | 0.8 (46.6) | 23.0 |
| −9.0 | 18.6 | 9.0 | −0.8 (−48.6) | 0.8 (48.6) | 24.0 |
| −9.7 | 19.0 | 9.7 | −0.9 (−50.6) | 0.9 (50.6) | 25.0 |
| −10.4 | 19.3 | 10.4 | −0.9 (−52.7) | 0.9 (52.7) | 26.0 |
| −11.0 | 19.5 | 11.0 | −1.0 (−54.7) | 1.0 (54.7) | 27.0 |
| −11.7 | 19.7 | 11.7 | −1.0 (−56.7) | 1.0 (56.7) | 28.0 |
| −12.4 | 19.9 | 12.4 | −1.0 (−58.7) | 1.0 (58.7) | 29.0 |
| −13.1 | 19.9 | 13.1 | −1.1 (−60.8) | 1.1 (60.8) | 30.0 |
| −13.8 | 20.0 | 13.8 | −1.1 (−62.8) | 1.1 (62.8) | 31.0 |

Note:
Theta and Phi shown in Radians & (Degrees)

APPENDIX B

| s | x | y | Theta | Phi | Cost |
|---|---|---|-------|-----|------|
| Generating Neighborhood of radius 28 mm | | | | | |
| Alpha Rotation of this thread = 0.0 (0.0) | | | | | |
| 0.0 | 1.0 | 0.0 | 0.0 (0.0) | 0.0 (2.0) | 1.0 |
| 0.0 | 2.0 | 0.1 | 0.0 (0.0) | 0.1 (4.1) | 2.0 |
| 0.0 | 3.0 | 0.2 | 0.0 (0.0) | 0.1 (6.1) | 3.0 |
| 0.0 | 4.0 | 0.3 | 0.0 (0.0) | 0.1 (8.2) | 4.0 |
| 0.0 | 5.0 | 0.4 | 0.0 (0.0) | 0.2 (10.2) | 5.0 |
| 0.0 | 6.0 | 0.6 | 0.0 (0.0) | 0.2 (12.3) | 6.0 |
| 0.0 | 6.9 | 0.9 | 0.0 (0.0) | 0.3 (14.3) | 7.0 |
| 0.0 | 7.9 | 1.1 | 0.0 (0.0) | 0.3 (16.4) | 8.0 |
| 0.0 | 8.8 | 1.4 | 0.0 (0.0) | 0.3 (18.4) | 9.0 |
| 0.0 | 9.8 | 1.8 | 0.0 (0.0) | 0.4 (20.5) | 10.0 |
| 0.0 | 10.7 | 2.1 | 0.0 (0.0) | 0.4 (22.5) | 11.0 |
| 0.0 | 11.6 | 2.5 | 0.0 (0.0) | 0.4 (24.6) | 12.0 |
| 0.0 | 12.5 | 3.0 | 0.0 (0.0) | 0.5 (26.6) | 13.0 |
| 0.0 | 13.4 | 3.4 | 0.0 (0.0) | 0.5 (28.6) | 14.0 |
| 0.0 | 14.3 | 3.9 | 0.0 (0.0) | 0.5 (30.7) | 15.0 |
| 0.0 | 15.1 | 4.4 | 0.0 (0.0) | 0.6 (32.7) | 16.0 |
| 0.0 | 16.0 | 5.0 | 0.0 (0.0) | 0.6 (34.8) | 17.0 |
| 0.0 | 16.8 | 5.6 | 0.0 (0.0) | 0.6 (36.8) | 18.0 |
| 0.0 | 17.6 | 6.2 | 0.0 (0.0) | 0.7 (38.9) | 19.0 |
| 0.0 | 18.3 | 6.8 | 0.0 (0.0) | 0.7 (40.9) | 20.0 |
| 0.0 | 19.1 | 7.5 | 0.0 (0.0) | 0.8 (43.0) | 21.0 |
| 0.0 | 19.8 | 8.2 | 0.0 (0.0) | 0.8 (45.0) | 22.0 |
| 0.0 | 20.5 | 8.9 | 0.0 (0.0) | 0.8 (47.1) | 23.0 |
| 0.0 | 21.2 | 9.7 | 0.0 (0.0) | 0.9 (49.1) | 24.0 |
| 0.0 | 21.8 | 10.4 | 0.0 (0.0) | 0.9 (51.2) | 25.0 |
| 0.0 | 22.4 | 11.2 | 0.0 (0.0) | 0.9 (53.2) | 26.0 |
| 0.0 | 23.0 | 12.0 | 0.0 (0.0) | 1.0 (55.2) | 27.0 |
| 0.0 | 23.6 | 12.9 | 0.0 (0.0) | 1.0 (57.3) | 28.0 |
| 0.0 | 24.1 | 13.7 | 0.0 (0.0) | 1.0 (59.3) | 29.0 |
| 0.0 | 24.6 | 14.6 | 0.0 (0.0) | 1.1 (61.4) | 30.0 |
| 0.0 | 25.0 | 15.5 | 0.0 (0.0) | 1.1 (63.4) | 31.0 |
| 0.0 | 25.5 | 16.4 | 0.0 (0.0) | 1.1 (65.5) | 32.0 |
| 0.0 | 25.9 | 17.3 | 0.0 (0.0) | 1.2 (67.5) | 33.0 |
| 0.0 | 26.2 | 18.2 | 0.0 (0.0) | 1.2 (69.6) | 34.0 |
| 0.0 | 26.6 | 19.2 | 0.0 (0.0) | 1.3 (71.6) | 35.0 |
| 0.0 | 26.9 | 20.1 | 0.0 (0.0) | 1.3 (73.7) | 36.0 |
| 0.0 | 27.1 | 21.1 | 0.0 (0.0) | 1.3 (75.7) | 37.0 |
| 0.0 | 27.4 | 22.1 | 0.0 (0.0) | 1.4 (77.8) | 38.0 |
| 0.0 | 27.6 | 23.0 | 0.0 (0.0) | 1.4 (79.8) | 39.0 |
| 0.0 | 27.7 | 24.0 | 0.0 (0.0) | 1.4 (81.9) | 40.0 |
| 0.0 | 27.8 | 25.0 | 0.0 (0.0) | 1.5 (83.9) | 41.0 |
| 0.0 | 27.9 | 26.0 | 0.0 (0.0) | 1.5 (85.9) | 42.0 |
| 0.0 | 28.0 | 27.0 | 0.0 (0.0) | 1.5 (88.0) | 43.0 |
| Alpha Rotation of this thread = 0.8 (45.0) | | | | | |
| 0.0 | 1.0 | 0.0 | 0.0 (1.4) | 0.0 (1.4) | 1.0 |
| 0.1 | 2.0 | 0.1 | 0.1 (2.9) | 0.1 (2.9) | 2.0 |
| 0.1 | 3.0 | 0.1 | 0.1 (4.3) | 0.1 (4.3) | 3.0 |
| 0.2 | 4.0 | 0.2 | 0.1 (5.8) | 0.1 (5.8) | 4.0 |
| 0.3 | 5.0 | 0.3 | 0.1 (7.2) | 0.1 (7.2) | 5.0 |
| 0.5 | 6.0 | 0.5 | 0.2 (8.7) | 0.2 (8.7) | 6.0 |
| 0.6 | 6.9 | 0.6 | 0.2 (10.1) | 0.2 (10.1) | 7.0 |
| 0.8 | 7.9 | 0.8 | 0.2 (11.6) | 0.2 (11.6) | 8.0 |
| 1.0 | 8.8 | 1.0 | 0.2 (13.0) | 0.2 (13.0) | 9.0 |
| 1.2 | 9.8 | 1.2 | 0.3 (14.5) | 0.3 (14.5) | 10.0 |
| 1.5 | 10.7 | 1.5 | 0.3 (15.9) | 0.3 (15.9) | 11.0 |
| 1.8 | 11.6 | 1.8 | 0.3 (17.4) | 0.3 (17.4) | 12.0 |
| 2.1 | 12.5 | 2.1 | 0.3 (18.8) | 0.3 (18.8) | 13.0 |
| 2.4 | 13.4 | 2.4 | 0.4 (20.3) | 0.4 (20.3) | 14.0 |
| 2.8 | 14.3 | 2.8 | 0.4 (21.7) | 0.4 (21.7) | 15.0 |

APPENDIX B-continued

| s | x | y | Theta | Phi | Cost |
|---|---|---|-------|-----|------|
| 3.1 | 15.1 | 3.1 | 0.4 (23.2) | 0.4 (23.2) | 16.0 |
| 3.5 | 16.0 | 3.5 | 0.4 (24.6) | 0.4 (24.6) | 17.0 |
| 4.0 | 16.8 | 4.0 | 0.5 (26.0) | 0.5 (26.0) | 18.0 |
| 4.4 | 17.6 | 4.4 | 0.5 (27.5) | 0.5 (27.5) | 19.0 |
| 4.8 | 18.3 | 4.8 | 0.5 (28.9) | 0.5 (28.9) | 20.0 |
| 5.3 | 19.1 | 5.3 | 0.5 (30.4) | 0.5 (30.4) | 21.0 |
| 5.8 | 19.8 | 5.8 | 0.6 (31.8) | 0.6 (31.8) | 22.0 |
| 6.3 | 20.5 | 6.3 | 0.6 (33.3) | 0.6 (33.3) | 23.0 |
| 6.8 | 21.2 | 6.8 | 0.6 (34.7) | 0.6 (34.7) | 24.0 |
| 7.4 | 21.8 | 7.4 | 0.6 (36.2) | 0.6 (36.2) | 25.0 |
| 7.9 | 22.4 | 7.9 | 0.7 (37.6) | 0.7 (37.6) | 26.0 |
| 8.5 | 23.0 | 8.5 | 0.7 (39.1) | 0.7 (39.1) | 27.0 |
| 9.1 | 23.6 | 9.1 | 0.7 (40.5) | 0.7 (40.5) | 28.0 |
| 9.7 | 24.1 | 9.7 | 0.7 (42.0) | 0.7 (42.0) | 29.0 |
| 10.3 | 24.6 | 10.3 | 0.8 (43.4) | 0.8 (43.4) | 30.0 |
| 10.9 | 25.0 | 10.9 | 0.8 (44.9) | 0.8 (44.9) | 31.0 |
| 11.6 | 25.5 | 11.6 | 0.8 (46.3) | 0.8 (46.3) | 32.0 |
| 12.2 | 25.9 | 12.2 | 0.8 (47.7) | 0.8 (47.7) | 33.0 |
| 12.9 | 26.2 | 12.9 | 0.9 (49.2) | 0.9 (49.2) | 34.0 |
| 13.6 | 26.6 | 13.6 | 0.9 (50.6) | 0.9 (50.6) | 35.0 |
| 14.2 | 26.9 | 14.2 | 0.9 (52.1) | 0.9 (52.1) | 36.0 |
| 14.9 | 27.1 | 14.9 | 0.9 (53.5) | 0.9 (53.5) | 37.0 |
| 15.6 | 27.4 | 15.6 | 1.0 (55.0) | 1.0 (55.0) | 38.0 |
| 16.3 | 27.6 | 16.3 | 1.0 (56.4) | 1.0 (56.4) | 39.0 |
| 17.0 | 27.7 | 17.0 | 1.0 (57.9) | 1.0 (57.9) | 40.0 |
| 17.7 | 27.8 | 17.7 | 1.0 (59.3) | 1.0 (59.3) | 41.0 |
| 18.4 | 27.9 | 18.4 | 1.1 (60.8) | 1.1 (60.8) | 42.0 |
| 19.1 | 28.0 | 19.1 | 1.1 (62.2) | 1.1 (62.2) | 43.0 |

Alpha Rotation of this thread = 1.6 (90.0)

| s | x | y | Theta | Phi | Cost |
|---|---|---|-------|-----|------|
| 0.0 | 1.0 | −0.0 | 0.0 (2.0) | −0.0 (−0.0) | 1.0 |
| 0.1 | 2.0 | −0.0 | 0.1 (4.1) | −0.0 (−0.0) | 2.0 |
| 0.2 | 3.0 | −0.0 | 0.1 (6.1) | −0.0 (−0.0) | 3.0 |
| 0.3 | 4.0 | −0.0 | 0.1 (8.2) | −0.0 (−0.0) | 4.0 |
| 0.4 | 5.0 | −0.0 | 0.2 (10.2) | −0.0 (−0.0) | 5.0 |
| 0.6 | 6.0 | −0.0 | 0.2 (12.3) | −0.0 (−0.0) | 6.0 |
| 0.9 | 6.9 | −0.0 | 0.3 (14.3) | −0.0 (−0.0) | 7.0 |
| 1.1 | 7.9 | −0.0 | 0.3 (16.4) | −0.0 (−0.0) | 8.0 |
| 1.4 | 8.8 | −0.0 | 0.3 (18.4) | −0.0 (−0.0) | 9.0 |
| 1.8 | 9.8 | −0.0 | 0.4 (20.5) | −0.0 (−0.0) | 10.0 |
| 2.1 | 10.7 | −0.0 | 0.4 (22.5) | −0.0 (−0.0) | 11.0 |
| 2.5 | 11.6 | −0.0 | 0.4 (24.6) | −0.0 (−0.0) | 12.0 |
| 3.0 | 12.5 | −0.0 | 0.5 (26.6) | −0.0 (−0.0) | 13.0 |
| 3.4 | 13.4 | −0.0 | 0.5 (28.6) | −0.0 (−0.0) | 14.0 |
| 3.9 | 14.3 | −0.0 | 0.5 (30.7) | −0.0 (−0.0) | 15.0 |
| 4.4 | 15.1 | −0.0 | 0.6 (32.7) | −0.0 (−0.0) | 16.0 |
| 5.0 | 16.0 | −0.0 | 0.6 (34.8) | −0.0 (−0.0) | 17.0 |
| 5.6 | 16.8 | −0.0 | 0.6 (36.8) | −0.0 (−0.0) | 18.0 |
| 6.2 | 17.6 | −0.0 | 0.7 (38.9) | −0.0 (−0.0) | 19.0 |
| 6.8 | 18.3 | −0.0 | 0.7 (40.9) | −0.0 (−0.0) | 20.0 |
| 7.5 | 19.1 | −0.0 | 0.8 (43.0) | −0.0 (−0.0) | 21.0 |
| 8.2 | 19.8 | −0.0 | 0.8 (45.0) | −0.0 (−0.0) | 22.0 |
| 8.9 | 20.5 | −0.0 | 0.8 (47.1) | −0.0 (−0.0) | 23.0 |
| 9.7 | 21.2 | −0.0 | 0.9 (49.1) | −0.0 (−0.0) | 24.0 |
| 10.4 | 21.8 | −0.0 | 0.9 (51.2) | −0.0 (−0.0) | 25.0 |
| 11.2 | 22.4 | −0.0 | 0.9 (53.2) | −0.0 (−0.0) | 26.0 |
| 12.0 | 23.0 | −0.0 | 1.0 (55.2) | −0.0 (−0.0) | 27.0 |
| 12.9 | 23.6 | −0.0 | 1.0 (57.3) | −0.0 (−0.0) | 28.0 |
| 13.7 | 24.1 | −0.0 | 1.0 (59.3) | −0.0 (−0.0) | 29.0 |
| 14.6 | 24.6 | −0.0 | 1.1 (61.4) | −0.0 (−0.0) | 30.0 |
| 15.5 | 25.0 | −0.0 | 1.1 (63.4) | −0.0 (−0.0) | 31.0 |
| 16.4 | 25.5 | −0.0 | 1.1 (65.5) | −0.0 (−0.0) | 32.0 |
| 17.3 | 25.9 | −0.0 | 1.2 (67.5) | −0.0 (−0.0) | 33.0 |
| 18.2 | 26.2 | −0.0 | 1.2 (69.6) | −0.0 (−0.0) | 34.0 |
| 19.2 | 26.6 | −0.0 | 1.3 (71.6) | −0.0 (−0.0) | 35.0 |
| 20.1 | 26.9 | −0.0 | 1.3 (73.7) | −0.0 (−0.0) | 36.0 |
| 21.1 | 27.1 | −0.0 | 1.3 (75.7) | −0.0 (−0.0) | 37.0 |
| 22.1 | 27.4 | −0.0 | 1.4 (77.8) | −0.0 (−0.0) | 38.0 |
| 23.0 | 27.6 | −0.0 | 1.4 (79.8) | −0.0 (−0.0) | 39.0 |
| 24.0 | 27.7 | −0.0 | 1.4 (81.9) | −0.0 (−0.0) | 40.0 |
| 25.0 | 27.8 | −0.0 | 1.5 (83.9) | −0.0 (−0.0) | 41.0 |
| 26.0 | 27.9 | −0.0 | 1.5 (85.9) | −0.0 (−0.0) | 42.0 |
| 27.0 | 28.0 | −0.0 | 1.5 (88.0) | −0.0 (−0.0) | 43.0 |

Alpha Rotation of this thread = 2.4 (135.0)

| s | x | y | Theta | Phi | Cost |
|---|---|---|-------|-----|------|
| 0.0 | 1.0 | −0.0 | 0.0 (1.4) | −0.0 (−1.4) | 1.0 |
| 0.1 | 2.0 | −0.1 | 0.1 (2.9) | −0.1 (−2.9) | 2.0 |
| 0.1 | 3.0 | −0.1 | 0.1 (4.3) | −0.1 (−4.3) | 3.0 |
| 0.2 | 4.0 | −0.2 | 0.1 (5.8) | −0.1 (−5.8) | 4.0 |
| 0.3 | 5.0 | −0.3 | 0.1 (7.2) | −0.1 (−7.2) | 5.0 |
| 0.5 | 6.0 | −0.5 | 0.2 (8.7) | −0.2 (−8.7) | 6.0 |
| 0.6 | 6.9 | −0.6 | 0.2 (10.1) | −0.2 (−10.1) | 7.0 |
| 0.8 | 7.9 | −0.8 | 0.2 (11.6) | −0.2 (−11.6) | 8.0 |
| 1.0 | 8.8 | −1.0 | 0.2 (13.0) | −0.2 (−13.0) | 9.0 |
| 1.2 | 9.8 | −1.2 | 0.3 (14.5) | −0.3 (−14.5) | 10.0 |
| 1.5 | 10.7 | −1.5 | 0.3 (15.9) | −0.3 (−15.9) | 11.0 |
| 1.8 | 11.6 | −1.8 | 0.3 (17.4) | −0.3 (−17.4) | 12.0 |
| 2.1 | 12.5 | −2.1 | 0.3 (18.8) | −0.3 (−18.8) | 13.0 |
| 2.4 | 13.4 | −2.4 | 0.4 (20.3) | −0.4 (−20.3) | 14.0 |
| 2.8 | 14.3 | −2.8 | 0.4 (21.7) | −0.4 (−21.7) | 15.0 |
| 3.1 | 15.1 | −3.1 | 0.4 (23.2) | −0.4 (−23.2) | 16.0 |
| 3.5 | 16.0 | −3.5 | 0.4 (24.6) | −0.4 (−24.6) | 17.0 |
| 4.0 | 16.8 | −4.0 | 0.5 (26.0) | −0.5 (−26.0) | 18.0 |
| 4.4 | 17.6 | −4.4 | 0.5 (27.5) | −0.5 (−27.5) | 19.0 |
| 4.8 | 18.3 | −4.8 | 0.5 (28.9) | −0.5 (−28.9) | 20.0 |
| 5.3 | 19.1 | −5.3 | 0.5 (30.4) | −0.5 (−30.4) | 21.0 |
| 5.8 | 19.8 | −5.8 | 0.6 (31.8) | −0.6 (−31.8) | 22.0 |
| 6.3 | 20.5 | −6.3 | 0.6 (33.3) | −0.6 (−33.3) | 23.0 |
| 6.8 | 21.2 | −6.8 | 0.6 (34.7) | −0.6 (−34.7) | 24.0 |
| 7.4 | 21.8 | −7.4 | 0.6 (36.2) | −0.6 (−36.2) | 25.0 |
| 7.9 | 22.4 | −7.9 | 0.7 (37.6) | −0.7 (−37.6) | 26.0 |
| 8.5 | 23.0 | −8.5 | 0.7 (39.1) | −0.7 (−39.1) | 27.0 |
| 9.1 | 23.6 | −9.1 | 0.7 (40.5) | −0.7 (−40.5) | 28.0 |
| 9.7 | 24.1 | −9.7 | 0.7 (42.0) | −0.7 (−42.0) | 29.0 |
| 10.3 | 24.6 | −10.3 | 0.8 (43.4) | −0.8 (−43.4) | 30.0 |
| 10.9 | 25.0 | −10.9 | 0.8 (44.9) | −0.8 (−44.9) | 31.0 |
| 11.6 | 25.5 | −11.6 | 0.8 (46.3) | −0.8 (−46.3) | 32.0 |
| 12.2 | 25.9 | −12.2 | 0.8 (47.7) | −0.8 (−47.7) | 33.0 |
| 12.9 | 26.2 | −12.9 | 0.9 (49.2) | −0.9 (−49.2) | 34.0 |
| 13.6 | 26.6 | −13.6 | 0.9 (50.6) | −0.9 (−50.6) | 35.0 |
| 14.2 | 26.9 | −14.2 | 0.9 (52.1) | −0.9 (−52.1) | 36.0 |
| 14.9 | 27.1 | −14.9 | 0.9 (53.5) | −0.9 (−53.5) | 37.0 |
| 15.6 | 27.4 | −15.6 | 1.0 (55.0) | −1.0 (−55.0) | 38.0 |
| 16.3 | 27.6 | −16.3 | 1.0 (56.4) | −1.0 (−56.4) | 39.0 |
| 17.0 | 27.7 | −17.0 | 1.0 (57.9) | −1.0 (−57.9) | 40.0 |
| 17.7 | 27.8 | −17.7 | 1.0 (59.3) | −1.0 (−59.3) | 41.0 |
| 18.4 | 27.9 | −18.4 | 1.1 (60.8) | −1.1 (−60.8) | 42.0 |
| 19.1 | 28.0 | −19.1 | 1.1 (62.2) | −1.1 (−62.2) | 43.0 |

Alpha Rotation of this thread = 3.1 (180.0)

| s | x | y | Theta | Phi | Cost |
|---|---|---|-------|-----|------|
| −0.0 | 1.0 | −0.0 | −0.0 (−0.0) | −0.0 (−2.0) | 1.0 |
| −0.0 | 2.0 | −0.1 | −0.0 (−0.0) | −0.1 (−4.1) | 2.0 |
| −0.0 | 3.0 | −0.2 | −0.0 (−0.0) | −0.1 (−6.1) | 3.0 |
| −0.0 | 4.0 | −0.3 | −0.0 (−0.0) | −0.1 (−8.2) | 4.0 |
| −0.0 | 5.0 | −0.4 | −0.0 (−0.0) | −0.2 (−10.2) | 5.0 |
| −0.0 | 6.0 | −0.6 | −0.0 (−0.0) | −0.2 (−12.3) | 6.0 |
| −0.0 | 6.9 | −0.9 | −0.0 (−0.0) | −0.3 (−14.3) | 7.0 |
| −0.0 | 7.9 | −1.1 | −0.0 (−0.0) | −0.3 (−16.4) | 8.0 |
| −0.0 | 8.8 | −1.4 | −0.0 (−0.0) | −0.3 (−18.4) | 9.0 |
| −0.0 | 9.8 | −1.8 | −0.0 (−0.0) | −0.4 (−20.5) | 10.0 |
| −0.0 | 10.7 | −2.1 | −0.0 (−0.0) | −0.4 (−22.5) | 11.0 |
| −0.0 | 11.6 | −2.5 | −0.0 (−0.0) | −0.4 (−24.6) | 12.0 |
| −0.0 | 12.5 | −3.0 | −0.0 (−0.0) | −0.5 (−26.6) | 13.0 |
| −0.0 | 13.4 | −3.4 | −0.0 (−0.0) | −0.5 (−28.6) | 14.0 |
| −0.0 | 14.3 | −3.9 | −0.0 (−0.0) | −0.5 (−30.7) | 15.0 |
| −0.0 | 15.1 | −4.4 | −0.0 (−0.0) | −0.6 (−32.7) | 16.0 |
| −0.0 | 16.0 | −5.0 | −0.0 (−0.0) | −0.6 (−34.8) | 17.0 |
| −0.0 | 16.8 | −5.6 | −0.0 (−0.0) | −0.6 (−36.8) | 18.0 |
| −0.0 | 17.6 | −6.2 | −0.0 (−0.0) | −0.7 (−38.9) | 19.0 |
| −0.0 | 18.3 | −6.8 | −0.0 (−0.0) | −0.7 (−40.9) | 20.0 |
| −0.0 | 19.1 | −7.5 | −0.0 (−0.0) | −0.8 (−43.0) | 21.0 |
| −0.0 | 19.8 | −8.2 | −0.0 (−0.0) | −0.8 (−45.0) | 22.0 |
| −0.0 | 20.5 | −8.9 | −0.0 (−0.0) | −0.8 (−47.1) | 23.0 |
| −0.0 | 21.2 | −9.7 | −0.0 (−0.0) | −0.9 (−49.1) | 24.0 |
| −0.0 | 21.8 | −10.4 | −0.0 (−0.0) | −0.9 (−51.2) | 25.0 |
| −0.0 | 22.4 | −11.2 | −0.0 (−0.0) | −0.9 (−53.2) | 26.0 |
| −0.0 | 23.0 | −12.0 | −0.0 (−0.0) | −1.0 (−55.2) | 27.0 |
| −0.0 | 23.6 | −12.9 | −0.0 (−0.0) | −1.0 (−57.3) | 28.0 |
| −0.0 | 24.1 | −13.7 | −0.0 (−0.0) | −1.0 (−59.3) | 29.0 |
| −0.0 | 24.6 | −14.6 | −0.0 (−0.0) | −1.1 (−61.4) | 30.0 |
| −0.0 | 25.0 | −15.5 | −0.0 (−0.0) | −1.1 (−63.4) | 31.0 |
| −0.0 | 25.5 | −16.4 | −0.0 (−0.0) | −1.1 (−65.5) | 32.0 |
| −0.0 | 25.9 | −17.3 | −0.0 (−0.0) | −1.2 (−67.5) | 33.0 |
| −0.0 | 26.2 | −18.2 | −0.0 (−0.0) | −1.2 (−69.6) | 34.0 |
| −0.0 | 26.6 | −19.2 | −0.0 (−0.0) | −1.3 (−71.6) | 35.0 |
| −0.0 | 26.9 | −20.1 | −0.0 (−0.0) | −1.3 (−73.7) | 36.0 |

APPENDIX B-continued

| s | x | y | Theta | Phi | Cost |
|---|---|---|---|---|---|
| −0.0 | 27.1 | −21.1 | −0.0 (−0.0) | −1.3 (−75.7) | 37.0 |
| −0.0 | 27.4 | −22.1 | −0.0 (−0.0) | −1.4 (−77.8) | 38.0 |
| −0.0 | 27.6 | −23.0 | −0.0 (−0.0) | −1.4 (−79.8) | 39.0 |
| −0.0 | 27.7 | −24.0 | −0.0 (−0.0) | −1.4 (−81.9) | 40.0 |
| −0.0 | 27.8 | −25.0 | −0.0 (−0.0) | −1.5 (−83.9) | 41.0 |
| −0.0 | 27.9 | −26.0 | −0.0 (−0.0) | −1.5 (−85.9) | 42.0 |
| −0.0 | 28.0 | −27.0 | −0.0 (−0.0) | −1.5 (−88.0) | 43.0 |
| Alpha Rotation of this thread = 3.9 (225.0) | | | | | |
| −0.0 | 1.0 | −0.0 | −0.0 (−1.4) | −0.0 (−1.4) | 1.0 |
| −0.1 | 2.0 | −0.1 | −0.1 (−2.9) | −0.1 (−2.9) | 2.0 |
| −0.1 | 3.0 | −0.1 | −0.1 (−4.3) | −0.1 (−4.3) | 3.0 |
| −0.2 | 4.0 | −0.2 | −0.1 (−5.8) | −0.1 (−5.8) | 4.0 |
| −0.3 | 5.0 | −0.3 | −0.1 (−7.2) | −0.1 (−7.2) | 5.0 |
| −0.5 | 6.0 | −0.5 | −0.2 (−8.7) | −0.2 (−8.7) | 6.0 |
| −0.6 | 6.9 | −0.6 | −0.2 (−10.1) | −0.2 (−10.1) | 7.0 |
| −0.8 | 7.9 | −0.8 | −0.2 (−11.6) | −0.2 (−11.6) | 8.0 |
| −1.0 | 8.8 | −1.0 | −0.2 (−13.0) | −0.2 (−13.0) | 9.0 |
| −1.2 | 9.8 | −1.2 | −0.3 (−14.5) | −0.3 (−14.5) | 10.0 |
| −1.5 | 10.7 | −1.5 | −0.3 (−15.9) | −0.3 (−15.9) | 11.0 |
| −1.8 | 11.6 | −1.8 | −0.3 (−17.4) | −0.3 (−17.4) | 12.0 |
| −2.1 | 12.5 | −2.1 | −0.3 (−18.8) | −0.3 (−18.8) | 13.0 |
| −2.4 | 13.4 | −2.4 | −0.4 (−20.3) | −0.4 (−20.3) | 14.0 |
| −2.8 | 14.3 | −2.8 | −0.4 (−21.7) | −0.4 (−21.7) | 15.0 |
| −3.1 | 15.1 | −3.1 | −0.4 (−23.2) | −0.4 (−23.2) | 16.0 |
| −3.5 | 16.0 | −3.5 | −0.4 (−24.6) | −0.4 (−24.6) | 17.0 |
| −4.0 | 16.8 | −4.0 | −0.5 (−26.0) | −0.5 (−26.0) | 18.0 |
| −4.4 | 17.6 | −4.4 | −0.5 (−27.5) | −0.5 (−27.5) | 19.0 |
| −4.8 | 18.3 | −4.8 | −0.5 (−28.9) | −0.5 (−28.9) | 20.0 |
| −5.3 | 19.1 | −5.3 | −0.5 (−30.4) | −0.5 (−30.4) | 21.0 |
| −5.8 | 19.8 | −5.8 | −0.6 (−31.8) | −0.6 (−31.8) | 22.0 |
| −6.3 | 20.5 | −6.3 | −0.6 (−33.3) | −0.6 (−33.3) | 23.0 |
| −6.8 | 21.2 | −6.8 | −0.6 (−34.7) | −0.6 (−34.7) | 24.0 |
| −7.4 | 21.8 | −7.4 | −0.6 (−36.2) | −0.6 (−36.2) | 25.0 |
| −7.9 | 22.4 | −7.9 | −0.7 (−37.6) | −0.7 (−37.6) | 26.0 |
| −8.5 | 23.0 | −8.5 | −0.7 (−39.1) | −0.7 (−39.1) | 27.0 |
| −9.1 | 23.6 | −9.1 | −0.7 (−40.5) | −0.7 (−40.5) | 28.0 |
| −9.7 | 24.1 | −9.7 | −0.7 (−42.0) | −0.7 (−42.0) | 29.0 |
| −10.3 | 24.6 | −10.3 | −0.8 (−43.4) | −0.8 (−43.4) | 30.0 |
| −10.9 | 25.0 | −10.9 | −0.8 (−44.9) | −0.8 (−44.9) | 31.0 |
| −11.6 | 25.5 | −11.6 | −0.8 (−46.3) | −0.8 (−46.3) | 32.0 |
| −12.2 | 25.9 | −12.2 | −0.8 (−47.7) | −0.8 (−47.7) | 33.0 |
| −12.9 | 26.2 | −12.9 | −0.9 (−49.2) | −0.9 (−49.2) | 34.0 |
| −13.6 | 26.6 | −13.6 | −0.9 (−50.6) | −0.9 (−50.6) | 35.0 |
| −14.2 | 26.9 | −14.2 | −0.9 (−52.1) | −0.9 (−52.1) | 36.0 |
| −14.9 | 27.1 | −14.9 | −0.9 (−53.5) | −0.9 (−53.5) | 37.0 |
| −15.6 | 27.4 | −15.6 | −1.0 (−55.0) | −1.0 (−55.0) | 38.0 |
| −16.3 | 27.6 | −16.3 | −1.0 (−56.4) | −1.0 (−56.4) | 39.0 |
| −17.0 | 27.7 | −17.0 | −1.0 (−57.9) | −1.0 (−57.9) | 40.0 |
| −17.7 | 27.8 | −17.7 | −1.0 (−59.3) | −1.0 (−59.3) | 41.0 |
| −18.4 | 27.9 | −18.4 | −1.1 (−60.8) | −1.1 (−60.8) | 42.0 |
| −19.1 | 28.0 | −19.1 | −1.1 (−62.2) | −1.1 (−62.2) | 43.0 |
| Alpha Rotation of this thread = 4.7 (270.0) | | | | | |
| −0.0 | 1.0 | 0.0 | −0.0 (−2.0) | 0.0 (0.0) | 1.0 |
| −0.1 | 2.0 | 0.0 | −0.1 (−4.1) | 0.0 (0.0) | 2.0 |
| −0.2 | 3.0 | 0.0 | −0.1 (−6.1) | 0.0 (0.0) | 3.0 |
| −0.3 | 4.0 | 0.0 | −0.1 (−8.2) | 0.0 (0.0) | 4.0 |
| −0.4 | 5.0 | 0.0 | −0.2 (−10.2) | 0.0 (0.0) | 5.0 |
| −0.6 | 6.0 | 0.0 | −0.2 (−12.3) | 0.0 (0.0) | 6.0 |
| −0.9 | 6.9 | 0.0 | −0.3 (−14.3) | 0.0 (0.0) | 7.0 |
| −1.1 | 7.9 | 0.0 | −0.3 (−16.4) | 0.0 (0.0) | 8.0 |
| −1.4 | 8.8 | 0.0 | −0.3 (−18.4) | 0.0 (0.0) | 9.0 |
| −1.8 | 9.8 | 0.0 | −0.4 (−20.5) | 0.0 (0.0) | 10.0 |
| −2.1 | 10.7 | 0.0 | −0.4 (−22.5) | 0.0 (0.0) | 11.0 |
| −2.5 | 11.6 | 0.0 | −0.4 (−24.6) | 0.0 (0.0) | 12.0 |
| −3.0 | 12.5 | 0.0 | −0.5 (−26.6) | 0.0 (0.0) | 13.0 |
| −3.4 | 13.4 | 0.0 | −0.5 (−28.6) | 0.0 (0.0) | 14.0 |
| −3.9 | 14.3 | 0.0 | −0.5 (−30.7) | 0.0 (0.0) | 15.0 |
| −4.4 | 15.1 | 0.0 | −0.6 (−32.7) | 0.0 (0.0) | 16.0 |
| −5.0 | 16.0 | 0.0 | −0.6 (−34.8) | 0.0 (0.0) | 17.0 |
| −5.6 | 16.8 | 0.0 | −0.6 (−36.8) | 0.0 (0.0) | 18.0 |
| −6.2 | 17.6 | 0.0 | −0.7 (−38.9) | 0.0 (0.0) | 19.0 |
| −6.8 | 18.3 | 0.0 | −0.7 (−40.9) | 0.0 (0.0) | 20.0 |
| −7.5 | 19.1 | 0.0 | −0.8 (−43.0) | 0.0 (0.0) | 21.0 |
| −8.2 | 19.8 | 0.0 | −0.8 (−45.0) | 0.0 (0.0) | 22.0 |
| −8.9 | 20.5 | 0.0 | −0.8 (−47.1) | 0.0 (0.0) | 23.0 |
| −9.7 | 21.2 | 0.0 | −0.9 (−49.1) | 0.0 (0.0) | 24.0 |
| −10.4 | 21.8 | 0.0 | −0.9 (−51.2) | 0.0 (0.0) | 25.0 |
| −11.2 | 22.4 | 0.0 | −0.9 (−53.2) | 0.0 (0.0) | 26.0 |
| −12.0 | 23.0 | 0.0 | −1.0 (−55.2) | 0.0 (0.0) | 27.0 |
| −12.9 | 23.6 | 0.0 | −1.0 (−57.3) | 0.0 (0.0) | 28.0 |
| −13.7 | 24.1 | 0.0 | −1.0 (−59.3) | 0.0 (0.0) | 29.0 |
| −14.6 | 24.6 | 0.0 | −1.1 (−61.4) | 0.0 (0.0) | 30.0 |
| −15.5 | 25.0 | 0.0 | −1.1 (−63.4) | 0.0 (0.0) | 31.0 |
| −16.4 | 25.5 | 0.0 | −1.1 (−65.5) | 0.0 (0.0) | 32.0 |
| −17.3 | 25.9 | 0.0 | −1.2 (−67.5) | 0.0 (0.0) | 33.0 |
| −18.2 | 26.2 | 0.0 | −1.2 (−69.6) | 0.0 (0.0) | 34.0 |
| −19.2 | 26.6 | 0.0 | −1.3 (−71.6) | 0.0 (0.0) | 35.0 |
| −20.1 | 26.9 | 0.0 | −1.3 (−73.7) | 0.0 (0.0) | 36.0 |
| −21.1 | 27.1 | 0.0 | −1.3 (−75.7) | 0.0 (0.0) | 37.0 |
| −22.1 | 27.4 | 0.0 | −1.4 (−77.8) | 0.0 (0.0) | 38.0 |
| −23.0 | 27.6 | 0.0 | −1.4 (−79.8) | 0.0 (0.0) | 39.0 |
| −24.0 | 27.7 | 0.0 | −1.4 (−81.9) | 0.0 (0.0) | 40.0 |
| −25.0 | 27.8 | 0.0 | −1.5 (−83.9) | 0.0 (0.0) | 41.0 |
| −26.0 | 27.9 | 0.0 | −1.5 (−85.9) | 0.0 (0.0) | 42.0 |
| −27.0 | 28.0 | 0.0 | −1.5 (−88.0) | 0.0 (0.0) | 43.0 |
| Alpha Rotation of this thread = 5.5 (315.0) | | | | | |
| −0.0 | 1.0 | 0.0 | −0.0 (−1.4) | 0.0 (1.4) | 1.0 |
| −0.1 | 2.0 | 0.1 | −0.1 (−2.9) | 0.1 (2.9) | 2.0 |
| −0.1 | 3.0 | 0.1 | −0.1 (−4.3) | 0.1 (4.3) | 3.0 |
| −0.2 | 4.0 | 0.2 | −0.1 (−5.8) | 0.1 (5.8) | 4.0 |
| −0.3 | 5.0 | 0.3 | −0.1 (−7.2) | 0.1 (7.2) | 5.0 |
| −0.5 | 6.0 | 0.5 | −0.2 (−8.7) | 0.2 (8.7) | 6.0 |
| −0.6 | 6.9 | 0.6 | −0.2 (−10.1) | 0.2 (10.1) | 7.0 |
| −0.8 | 7.9 | 0.8 | −0.2 (−11.6) | 0.2 (11.6) | 8.0 |
| −1.0 | 8.8 | 1.0 | −0.2 (−13.0) | 0.2 (13.0) | 9.0 |
| −1.2 | 9.8 | 1.2 | −0.3 (−14.5) | 0.3 (14.5) | 10.0 |
| −1.5 | 10.7 | 1.5 | −0.3 (−15.9) | 0.3 (15.9) | 11.0 |
| −1.8 | 11.6 | 1.8 | −0.3 (−17.4) | 0.3 (17.4) | 12.0 |
| −2.1 | 12.5 | 2.1 | −0.3 (−18.8) | 0.3 (18.8) | 13.0 |
| −2.4 | 13.4 | 2.4 | −0.4 (−20.3) | 0.4 (20.3) | 14.0 |
| −2.8 | 14.3 | 2.8 | −0.4 (−21.7) | 0.4 (21.7) | 15.0 |
| −3.1 | 15.1 | 3.1 | −0.4 (−23.2) | 0.4 (23.2) | 16.0 |
| −3.5 | 16.0 | 3.5 | −0.4 (−24.6) | 0.4 (24.6) | 17.0 |
| −4.0 | 16.8 | 4.0 | −0.5 (−26.0) | 0.5 (26.0) | 18.0 |
| −4.4 | 17.6 | 4.4 | −0.5 (−27.5) | 0.5 (27.5) | 19.0 |
| −4.8 | 18.3 | 4.8 | −0.5 (−28.9) | 0.5 (28.9) | 20.0 |
| −5.3 | 19.1 | 5.3 | −0.5 (−30.4) | 0.5 (30.4) | 21.0 |
| −5.8 | 19.8 | 5.8 | −0.6 (−31.8) | 0.6 (31.8) | 22.0 |
| −6.3 | 20.5 | 6.3 | −0.6 (−33.3) | 0.6 (33.3) | 23.0 |
| −6.8 | 21.2 | 6.8 | −0.6 (−34.7) | 0.6 (34.7) | 24.0 |
| −7.4 | 21.8 | 7.4 | −0.6 (−36.2) | 0.6 (36.2) | 25.0 |
| −7.9 | 22.4 | 7.9 | −0.7 (−37.6) | 0.7 (37.6) | 26.0 |
| −8.5 | 23.0 | 8.5 | −0.7 (−39.1) | 0.7 (39.1) | 27.0 |
| −9.1 | 23.6 | 9.1 | −0.7 (−40.5) | 0.7 (40.5) | 28.0 |
| −9.7 | 24.1 | 9.7 | −0.7 (−42.0) | 0.7 (42.0) | 29.0 |
| −10.3 | 24.6 | 10.3 | −0.8 (−43.4) | 0.8 (43.4) | 30.0 |
| −10.9 | 25.0 | 10.9 | −0.8 (−44.9) | 0.8 (44.9) | 31.0 |
| −11.6 | 25.5 | 11.6 | −0.8 (−46.3) | 0.8 (46.3) | 32.0 |
| −12.2 | 25.9 | 12.2 | −0.8 (−47.7) | 0.8 (47.7) | 33.0 |
| −12.9 | 26.2 | 12.9 | −0.9 (−49.2) | 0.9 (49.2) | 34.0 |
| −13.6 | 26.6 | 13.6 | −0.9 (−50.6) | 0.9 (50.6) | 35.0 |
| −14.2 | 26.9 | 14.2 | −0.9 (−52.1) | 0.9 (52.1) | 36.0 |
| −14.9 | 27.1 | 14.9 | −0.9 (−53.5) | 0.9 (53.5) | 37.0 |
| −15.6 | 27.4 | 15.6 | −1.0 (−55.0) | 1.0 (55.0) | 38.0 |
| −16.3 | 27.6 | 16.3 | −1.0 (−56.4) | 1.0 (56.4) | 39.0 |
| −17.0 | 27.7 | 17.0 | −1.0 (−57.9) | 1.0 (57.9) | 40.0 |
| −17.7 | 27.8 | 17.7 | −1.0 (−59.3) | 1.0 (59.3) | 41.0 |
| −18.4 | 27.9 | 18.4 | −1.1 (−60.8) | 1.1 (60.8) | 42.0 |
| −19.1 | 28.0 | 19.1 | −1.1 (−62.2) | 1.1 (62.2) | 43.0 |
| Generating Neighborhood of radius 14 mm | | | | | |
| Alpha Rotation of this thread = 0.0 (0.0) | | | | | |
| 0.0 | 1.0 | 0.0 | 0.0 (0.0) | 0.1 (4.1) | 7.0 |
| 0.0 | 2.0 | 0.1 | 0.0 (0.0) | 0.1 (8.2) | 14.0 |
| 0.0 | 3.0 | 0.3 | 0.0 (0.0) | 0.2 (12.3) | 21.0 |
| 0.0 | 3.9 | 0.6 | 0.0 (0.0) | 0.3 (16.4) | 28.0 |
| 0.0 | 4.9 | 0.9 | 0.0 (0.0) | 0.4 (20.5) | 35.0 |
| 0.0 | 5.8 | 1.3 | 0.0 (0.0) | 0.4 (24.6) | 42.0 |
| 0.0 | 6.7 | 1.7 | 0.0 (0.0) | 0.5 (28.6) | 49.0 |
| 0.0 | 7.6 | 2.2 | 0.0 (0.0) | 0.6 (32.7) | 56.0 |
| 0.0 | 8.4 | 2.8 | 0.0 (0.0) | 0.6 (36.8) | 63.0 |

APPENDIX B-continued

| s | x | y | Theta | Phi | Cost |
|---|---|---|---|---|---|
| 0.0 | 9.2 | 3.4 | 0.0 (0.0) | 0.7 (40.9) | 70.0 |
| 0.0 | 9.9 | 4.1 | 0.0 (0.0) | 0.8 (45.0) | 77.0 |
| 0.0 | 10.6 | 4.8 | 0.0 (0.0) | 0.9 (49.1) | 84.0 |
| 0.0 | 11.2 | 5.6 | 0.0 (0.0) | 0.9 (53.2) | 91.0 |
| 0.0 | 11.8 | 6.4 | 0.0 (0.0) | 1.0 (57.3) | 98.0 |
| 0.0 | 12.3 | 7.3 | 0.0 (0.0) | 1.1 (61.4) | 105.0 |
| 0.0 | 12.7 | 8.2 | 0.0 (0.0) | 1.1 (65.5) | 112.0 |
| 0.0 | 13.1 | 9.1 | 0.0 (0.0) | 1.2 (69.6) | 119.0 |
| 0.0 | 13.4 | 10.1 | 0.0 (0.0) | 1.3 (73.7) | 126.0 |
| 0.0 | 13.7 | 11.0 | 0.0 (0.0) | 1.4 (77.8) | 133.0 |
| 0.0 | 13.9 | 12.0 | 0.0 (0.0) | 1.4 (81.9) | 140.0 |
| 0.0 | 14.0 | 13.0 | 0.0 (0.0) | 1.5 (85.9) | 147.0 |
| Alpha Rotation of this thread = 0.8 (45.0) | | | | | |
| 0.0 | 1.0 | 0.0 | 0.1 (2.9) | 0.1 (2.9) | 7.0 |
| 0.1 | 2.0 | 0.1 | 0.1 (5.8) | 0.1 (5.8) | 14.0 |
| 0.2 | 3.0 | 0.2 | 0.2 (8.7) | 0.2 (8.7) | 21.0 |
| 0.4 | 3.9 | 0.4 | 0.2 (11.6) | 0.2 (11.6) | 28.0 |
| 0.6 | 4.9 | 0.6 | 0.3 (14.5) | 0.3 (14.5) | 35.0 |
| 0.9 | 5.8 | 0.9 | 0.3 (17.4) | 0.3 (17.4) | 42.0 |
| 1.2 | 6.7 | 1.2 | 0.4 (20.3) | 0.4 (20.3) | 49.0 |
| 1.6 | 7.6 | 1.6 | 0.4 (23.2) | 0.4 (23.2) | 56.0 |
| 2.0 | 8.4 | 2.0 | 0.5 (26.0) | 0.5 (26.0) | 63.0 |
| 2.4 | 9.2 | 2.4 | 0.5 (28.9) | 0.5 (28.9) | 70.0 |
| 2.9 | 9.9 | 2.9 | 0.6 (31.8) | 0.6 (31.8) | 77.0 |
| 3.4 | 10.6 | 3.4 | 0.6 (34.7) | 0.6 (34.7) | 84.0 |
| 4.0 | 11.2 | 4.0 | 0.7 (37.6) | 0.7 (37.6) | 91.0 |
| 4.6 | 11.8 | 4.6 | 0.7 (40.5) | 0.7 (40.5) | 98.0 |
| 5.2 | 12.3 | 5.2 | 0.8 (43.4) | 0.8 (43.4) | 105.0 |
| 5.8 | 12.7 | 5.8 | 0.8 (46.3) | 0.8 (46.3) | 112.0 |
| 6.4 | 13.1 | 6.4 | 0.9 (49.2) | 0.9 (49.2) | 119.0 |
| 7.1 | 13.4 | 7.1 | 0.9 (52.1) | 0.9 (52.1) | 126.0 |
| 7.8 | 13.7 | 7.8 | 1.0 (55.0) | 1.0 (55.0) | 133.0 |
| 8.5 | 13.9 | 8.5 | 1.0 (57.9) | 1.0 (57.9) | 140.0 |
| 9.2 | 14.0 | 9.2 | 1.1 (60.8) | 1.1 (60.8) | 147.0 |
| Alpha Rotation of this thread = 1.6 (90.0) | | | | | |
| 0.0 | 1.0 | −0.0 | 0.1 (4.1) | −0.0 (−0.0) | 7.0 |
| 0.1 | 2.0 | −0.0 | 0.1 (8.2) | −0.0 (−0.0) | 14.0 |
| 0.3 | 3.0 | −0.0 | 0.2 (12.3) | −0.0 (−0.0) | 21.0 |
| 0.6 | 3.9 | −0.0 | 0.3 (16.4) | −0.0 (−0.0) | 28.0 |
| 0.9 | 4.9 | −0.0 | 0.4 (20.5) | −0.0 (−0.0) | 35.0 |
| 1.3 | 5.8 | −0.0 | 0.4 (24.6) | −0.0 (−0.0) | 42.0 |
| 1.7 | 6.7 | −0.0 | 0.5 (28.6) | −0.0 (−0.0) | 49.0 |
| 2.2 | 7.6 | −0.0 | 0.6 (32.7) | −0.0 (−0.0) | 56.0 |
| 2.8 | 8.4 | −0.0 | 0.6 (36.8) | −0.0 (−0.0) | 63.0 |
| 3.4 | 9.2 | −0.0 | 0.7 (40.9) | −0.0 (−0.0) | 70.0 |
| 4.1 | 9.9 | −0.0 | 0.8 (45.0) | −0.0 (−0.0) | 77.0 |
| 4.8 | 10.6 | −0.0 | 0.9 (49.1) | −0.0 (−0.0) | 84.0 |
| 5.6 | 11.2 | −0.0 | 0.9 (53.2) | −0.0 (−0.0) | 91.0 |
| 6.4 | 11.8 | −0.0 | 1.0 (57.3) | −0.0 (−0.0) | 98.0 |
| 7.3 | 12.3 | −0.0 | 1.1 (61.4) | −0.0 (−0.0) | 105.0 |
| 8.2 | 12.7 | −0.0 | 1.1 (65.5) | −0.0 (−0.0) | 112.0 |
| 9.1 | 13.1 | −0.0 | 1.2 (69.6) | −0.0 (−0.0) | 119.0 |
| 10.1 | 13.4 | −0.0 | 1.3 (73.7) | −0.0 (−0.0) | 126.0 |
| 11.0 | 13.7 | −0.0 | 1.4 (77.8) | −0.0 (−0.0) | 133.0 |
| 12.0 | 13.9 | −0.0 | 1.4 (81.9) | −0.0 (−0.0) | 140.0 |
| 13.0 | 14.0 | −0.0 | 1.5 (85.9) | −0.0 (−0.0) | 147.0 |
| Alpha Rotation of this thread = 2.4 (135.0) | | | | | |
| 0.0 | 1.0 | −0.0 | 0.1 (2.9) | −0.1 (−2.9) | 7.0 |
| 0.1 | 2.0 | −0.1 | 0.1 (5.8) | −0.1 (−5.8) | 14.0 |
| 0.2 | 3.0 | −0.2 | 0.2 (8.7) | −0.2 (−8.7) | 21.0 |
| 0.4 | 3.9 | −0.4 | 0.2 (11.6) | −0.2 (−11.6) | 28.0 |
| 0.6 | 4.9 | −0.6 | 0.3 (14.5) | −0.3 (−14.5) | 35.0 |
| 0.9 | 5.8 | −0.9 | 0.3 (17.4) | −0.3 (−17.4) | 42.0 |
| 1.2 | 6.7 | −1.2 | 0.4 (20.3) | −0.4 (−20.3) | 49.0 |
| 1.6 | 7.6 | −1.6 | 0.4 (23.2) | −0.4 (−23.2) | 56.0 |
| 2.0 | 8.4 | −2.0 | 0.5 (26.0) | −0.5 (−26.0) | 63.0 |
| 2.4 | 9.2 | −2.4 | 0.5 (28.9) | −0.5 (−28.9) | 70.0 |
| 2.9 | 9.9 | −2.9 | 0.6 (31.8) | −0.6 (−31.8) | 77.0 |
| 3.4 | 10.6 | −3.4 | 0.6 (34.7) | −0.6 (−34.7) | 84.0 |
| 4.0 | 11.2 | −4.0 | 0.7 (37.6) | −0.7 (−37.6) | 91.0 |
| 4.6 | 11.8 | −4.6 | 0.7 (40.5) | −0.7 (−40.5) | 98.0 |
| 5.2 | 12.3 | −5.2 | 0.8 (43.4) | −0.8 (−43.4) | 105.0 |
| 5.8 | 12.7 | −5.8 | 0.8 (46.3) | −0.8 (−46.3) | 112.0 |
| 6.4 | 13.1 | −6.4 | 0.9 (49.2) | −0.9 (−49.2) | 119.0 |
| 7.1 | 13.4 | −7.1 | 0.9 (52.1) | −0.9 (−52.1) | 126.0 |
| 7.8 | 13.7 | −7.8 | 1.0 (55.0) | −1.0 (−55.0) | 133.0 |
| 8.5 | 13.9 | −8.5 | 1.0 (57.9) | −1.0 (−57.9) | 140.0 |
| 9.2 | 14.0 | −9.2 | 1.1 (60.8) | −1.1 (−60.8) | 147.0 |
| Alpha Rotation of this thread = 3.1 (180.0) | | | | | |
| −0.0 | 1.0 | −0.0 | −0.0 (−0.0) | −0.1 (−4.1) | 7.0 |
| −0.0 | 2.0 | −0.1 | −0.0 (−0.0) | −0.1 (−8.2) | 14.0 |
| −0.0 | 3.0 | −0.3 | −0.0 (−0.0) | −0.2 (−12.3) | 21.0 |
| −0.0 | 3.9 | −0.6 | −0.0 (−0.0) | −0.3 (−16.4) | 28.0 |
| −0.0 | 4.9 | −0.9 | −0.0 (−0.0) | −0.4 (−20.5) | 35.0 |
| −0.0 | 5.8 | −1.3 | −0.0 (−0.0) | −0.4 (−24.6) | 42.0 |
| −0.0 | 6.7 | −1.7 | −0.0 (−0.0) | −0.5 (−28.6) | 49.0 |
| −0.0 | 7.6 | −2.2 | −0.0 (−0.0) | −0.6 (−32.7) | 56.0 |
| −0.0 | 8.4 | −2.8 | −0.0 (−0.0) | −0.6 (−36.8) | 63.0 |
| −0.0 | 9.2 | −3.4 | −0.0 (−0.0) | −0.7 (−40.9) | 70.0 |
| −0.0 | 9.9 | −4.1 | −0.0 (−0.0) | −0.8 (−45.0) | 77.0 |
| −0.0 | 10.6 | −4.8 | −0.0 (−0.0) | −0.9 (−49.1) | 84.0 |
| −0.0 | 11.2 | −5.6 | −0.0 (−0.0) | −0.9 (−53.2) | 91.0 |
| −0.0 | 11.8 | −6.4 | −0.0 (−0.0) | −1.0 (−57.3) | 98.0 |
| −0.0 | 12.3 | −7.3 | −0.0 (−0.0) | −1.1 (−61.4) | 105.0 |
| −0.0 | 12.7 | −8.2 | −0.0 (−0.0) | −1.1 (−65.5) | 112.0 |
| −0.0 | 13.1 | −9.1 | −0.0 (−0.0) | −1.2 (−69.6) | 119.0 |
| −0.0 | 13.4 | −10.1 | −0.0 (−0.0) | −1.3 (−73.7) | 126.0 |
| −0.0 | 13.7 | −11.0 | −0.0 (−0.0) | −1.4 (−77.8) | 133.0 |
| −0.0 | 13.9 | −12.0 | −0.0 (−0.0) | −1.4 (−81.9) | 140.0 |
| −0.0 | 14.0 | −13.0 | −0.0 (−0.0) | −1.5 (−85.9) | 147.0 |
| Alpha Rotation of this thread = 3.9 (225.0) | | | | | |
| −0.0 | 1.0 | −0.0 | −0.1 (−2.9) | −0.1 (−2.9) | 7.0 |
| −0.1 | 2.0 | −0.1 | −0.1 (−5.8) | −0.1 (−5.8) | 14.0 |
| −0.2 | 3.0 | −0.2 | −0.2 (−8.7) | −0.2 (−8.7) | 21.0 |
| −0.4 | 3.9 | −0.4 | −0.2 (−11.6) | −0.2 (−11.6) | 28.0 |
| −0.6 | 4.9 | −0.6 | −0.3 (−14.5) | −0.3 (−14.5) | 35.0 |
| −0.9 | 5.8 | −0.9 | −0.3 (−17.4) | −0.3 (−17.4) | 42.0 |
| −1.2 | 6.7 | −1.2 | −0.4 (−20.3) | −0.4 (−20.3) | 49.0 |
| −1.6 | 7.6 | −1.6 | −0.4 (−23.2) | −0.4 (−23.2) | 56.0 |
| −2.0 | 8.4 | −2.0 | −0.5 (−26.0) | −0.5 (−26.0) | 63.0 |
| −2.4 | 9.2 | −2.4 | −0.5 (−28.9) | −0.5 (−28.9) | 70.0 |
| −2.9 | 9.9 | −2.9 | −0.6 (−31.8) | −0.6 (−31.8) | 77.0 |
| −3.4 | 10.6 | −3.4 | −0.6 (−34.7) | −0.6 (−34.7) | 84.0 |
| −4.0 | 11.2 | −4.0 | −0.7 (−37.6) | −0.7 (−37.6) | 91.0 |
| −4.6 | 11.8 | −4.6 | −0.7 (−40.5) | −0.7 (−40.5) | 98.0 |
| −5.2 | 12.3 | −5.2 | −0.8 (−43.4) | −0.8 (−43.4) | 105.0 |
| −5.8 | 12.7 | −5.8 | −0.8 (−46.3) | −0.8 (−46.3) | 112.0 |
| −6.4 | 13.1 | −6.4 | −0.9 (−49.2) | −0.9 (−49.2) | 119.0 |
| −7.1 | 13.4 | −7.1 | −0.9 (−52.1) | −0.9 (−52.1) | 126.0 |
| −7.8 | 13.7 | −7.8 | −1.0 (−55.0) | −1.0 (−55.0) | 133.0 |
| −8.5 | 13.9 | −8.5 | −1.0 (−57.9) | −1.0 (−57.9) | 140.0 |
| −9.2 | 14.0 | −9.2 | −1.1 (−60.8) | −1.1 (−60.8) | 147.0 |
| Alpha Rotation of this thread = 4.7 (270.0) | | | | | |
| −0.0 | 1.0 | 0.0 | −0.1 (−4.1) | 0.0 (0.0) | 7.0 |
| −0.1 | 2.0 | 0.0 | −0.1 (−8.2) | 0.0 (0.0) | 14.0 |
| −0.3 | 3.0 | 0.0 | −0.2 (−12.3) | 0.0 (0.0) | 21.0 |
| −0.6 | 3.9 | 0.0 | −0.3 (−16.4) | 0.0 (0.0) | 28.0 |
| −0.9 | 4.9 | 0.0 | −0.4 (−20.5) | 0.0 (0.0) | 35.0 |
| −1.3 | 5.8 | 0.0 | −0.4 (−24.6) | 0.0 (0.0) | 42.0 |
| −1.7 | 6.7 | 0.0 | −0.5 (−28.6) | 0.0 (0.0) | 49.0 |
| −2.2 | 7.6 | 0.0 | −0.6 (−32.7) | 0.0 (0.0) | 56.0 |
| −2.8 | 8.4 | 0.0 | −0.6 (−36.8) | 0.0 (0.0) | 63.0 |
| −3.4 | 9.2 | 0.0 | −0.7 (−40.9) | 0.0 (0.0) | 70.0 |
| −4.1 | 9.9 | 0.0 | −0.8 (−45.0) | 0.0 (0.0) | 77.0 |
| −4.8 | 10.6 | 0.0 | −0.9 (−49.1) | 0.0 (0.0) | 84.0 |
| −5.6 | 11.2 | 0.0 | −0.9 (−53.2) | 0.0 (0.0) | 91.0 |
| −6.4 | 11.8 | 0.0 | −1.0 (−57.3) | 0.0 (0.0) | 98.0 |
| −7.3 | 12.3 | 0.0 | −1.1 (−61.4) | 0.0 (0.0) | 105.0 |
| −8.2 | 12.7 | 0.0 | −1.1 (−65.5) | 0.0 (0.0) | 112.0 |
| −9.1 | 13.1 | 0.0 | −1.2 (−69.6) | 0.0 (0.0) | 119.0 |
| −10.1 | 13.4 | 0.0 | −1.3 (−73.7) | 0.0 (0.0) | 126.0 |
| −11.0 | 13.7 | 0.0 | −1.4 (−77.8) | 0.0 (0.0) | 133.0 |
| −12.0 | 13.9 | 0.0 | −1.4 (−81.9) | 0.0 (0.0) | 140.0 |
| −13.0 | 14.0 | 0.0 | −1.5 (−85.9) | 0.0 (0.0) | 147.0 |
| Alpha Rotation of this thread = 5.5 (315.0) | | | | | |
| −0.0 | 1.0 | 0.0 | −0.1 (−2.9) | 0.1 (2.9) | 7.0 |
| −0.1 | 2.0 | 0.1 | −0.1 (−5.8) | 0.1 (5.8) | 14.0 |
| −0.2 | 3.0 | 0.2 | −0.2 (−8.7) | 0.2 (8.7) | 21.0 |
| −0.4 | 3.9 | 0.4 | −0.2 (−11.6) | 0.2 (11.6) | 28.0 |

APPENDIX B-continued

| s | x | y | Theta | Phi | Cost |
|---|---|---|---|---|---|
| −0.6 | 4.9 | 0.6 | −0.3 (−14.5) | 0.3 (14.5) | 35.0 |
| −0.9 | 5.8 | 0.9 | −0.3 (−17.4) | 0.3 (17.4) | 42.0 |
| −1.2 | 6.7 | 1.2 | −0.4 (−20.3) | 0.4 (20.3) | 49.0 |
| −1.6 | 7.6 | 1.6 | −0.4 (−23.2) | 0.4 (23.2) | 56.0 |
| −2.0 | 8.4 | 2.0 | −0.5 (−26.0) | 0.5 (26.0) | 63.0 |
| −2.4 | 9.2 | 2.4 | −0.5 (−28.9) | 0.5 (28.9) | 70.0 |
| −2.9 | 9.9 | 2.9 | −0.6 (−31.8) | 0.6 (31.8) | 77.0 |
| −3.4 | 10.6 | 3.4 | −0.6 (−34.7) | 0.6 (34.7) | 84.0 |
| −4.0 | 11.2 | 4.0 | −0.7 (−37.6) | 0.7 (37.6) | 91.0 |
| −4.6 | 11.8 | 4.6 | −0.7 (−40.5) | 0.7 (40.5) | 98.0 |
| −5.2 | 12.3 | 5.2 | −0.8 (−43.4) | 0.8 (43.4) | 105.0 |
| −5.8 | 12.7 | 5.8 | −0.8 (−46.3) | 0.8 (46.3) | 112.0 |
| −6.4 | 13.1 | 6.4 | −0.9 (−49.2) | 0.9 (49.2) | 119.0 |
| −7.1 | 13.4 | 7.1 | −0.9 (−52.1) | 0.9 (52.1) | 126.0 |
| −7.8 | 13.7 | 7.8 | −1.0 (−55.0) | 1.0 (55.0) | 133.0 |
| −8.5 | 13.9 | 8.5 | −1.0 (−57.9) | 1.0 (57.9) | 140.0 |
| −9.2 | 14.0 | 9.2 | −1.1 (−60.8) | 1.1 (60.8) | 147.0 |

Note:
Theta and Phi shown in Radians & (Degrees)

We claim:

1. A system (1600) for determining at least one path for a non-holonomic physical tool (1604) having a directable tip (1605), comprising:
at least one computer readable memory (1608) to store physical pose information of a plurality of nodes each at a different discrete location in a physical task space, said plurality of nodes including at least one goal node that corresponds to a desired physical goal pose of the directable tip of the non-holonomic physical tool when the directable tip (1605) of the non-holonomic physical tool is located at the goal node; and
at least one digital data processing unit (1600) coupled to or including the at least one computer readable memory (1608), the at least one digital data processing unit (1600) including:
a neighborhood generation module (730) to generate and store in the memory (1608) a neighborhood of a physical task space node comprising at least one neighbor node thereof, said physical task space node and neighbor node having at least one permissible transition direction therebetween;
a transition cost calculation module (1603) to calculate and store in the memory (1608) the cost from the physical task space node to the at least one generated neighbor node along the at least one permissible transition direction therebetween;
a cost wave propagation module (770) to propagate at least one calculated cost wave from the at least one goal node and assign to each physical task space node and store in the memory (1608) a cost value and a direction of transition corresponding to a physical least cost path from a physical pose of the directable tip (1605) corresponding to the physical task space node to the physical goal pose; and
a path determination module (700) for determination and identification in the memory (1608) of a path (1606) comprising a sequence of physical task space nodes along the physical least cost path beginning at a start pose comprising a physical task space node corresponding to a physical natural/resting pose of the directable tip (1605) of the non-holonomic physical tool (1604) at a start location and following the physical least cost path therefrom in the permissible transition direction from the start node to successive nodes thereof to the goal node.

2. The system (1600) of claim 1, wherein the directable tip (1605) of the non-holonomic physical tool (1604) is further configured to follow the determined path stored in the memory (1606) by successively transitioning between physical task space nodes of the sequence, assuming the pose of each physical task space node in the sequence from the resting pose at the start location to the goal pose at the goal node.

3. The system (1600) of claim 1, wherein the neighborhood generation module (730) is further configured such that:
the at least one neighbor node comprises 6 dimensions including 3 positional values and 3 orientation values, and
the at least one neighbor node is stored in the memory (1608) as a change in each of the 3 positional values and 3 orientations from a node to the neighbor node.

4. The system (1600) of claim 1, further configured to simulate the sequence of physical task space nodes (1606) as a motion of the non-holonomic physical tool along the physical path stored in the memory (1608) wherein each node is a pose of the directable tip (1605) of the non-holonomic physical tool (1604).

5. The system (1600) of claim wherein a seed node for a determination and identification of the path is a starting node.

6. The system (1600) of claim 1, wherein a seed node for a determination and identification of the path is a goal node.

7. The system of (1600) claim 1, wherein:
the non-holonomic physical tool (1604) is a catheter (1000); and
the sequence of physical task space nodes (1606) corresponds to a sequence of blood vessel locations derived from patient morphology.

8. The system (1600) of claim 1, wherein:
the non-holonomic physical tool (1604) is selected from the group consisting of endoscope, bronchoscope (100), catheter (1001), cardiac ablation catheter (1101), and beveled needle (1500); and
the sequence of physical task space nodes (1606) corresponds to a sequence of passageway locations derived from patient morphology.

9. The system (1600) of claim 1, wherein the system stores the sequence (1606) in memory (1608) for access to the sequence (1606) by an interventionalist (1602) that is operating the non-holonomic physical tool.

10. The system (1600) of claim 1, wherein the system stores the sequence (1606) in memory (1608) for access to the sequence (1606) by an automated controller (1607) that is automatically operating the non-holonomic physical tool.

11. An apparatus (1700) for planning a physical least cost path for a non-holonomic physical tool (1604) having a directable tip (1605), comprising:
at least one computer readable storage medium (1608) for storing information embodying a discretized data structure representation of a physical task space that surrounds a location of the directable tip (1605) of the non-holonomic physical tool (1604) and comprises poses assumable by the directable tip (1605) in the physical task space represented in the physical task space as 3 position values and 3 orientations (1605) and representing the pose at each reachable neighbor thereof as a change comprising changes in the 3 positional values and the 3 orientations of the directable tip (1605) required to transition to a reachable neighbor; and
at least one digital data processing unit (1600) coupled to or including the at least one computer readable memory (1608), the at least one digital data processing unit (1600) including a plurality of module configured for:

assigning a cost to at least one neighboring position of a given position of the directable tip (1605) in the physical task space, based on a measure (1603) which varies according to position within the discretized data structure representation, the cost corresponding to at least one physical aspect of the physical task space, so that a cost from the at least one neighboring position to the given position is established;

starting the assigning of the cost at a start position;

causing the assigning of the cost to iterate, so that all reachable positions within the discretized representation are assigned respective costs, in waves propagating toward the start position from a goal position; and identifying a least cost path between the start position and the goal position in the discretized representation based on the assigned costs.

12. A method (700) for determining at least one physical motion specification for a non-holonomic physical tool (1604) having a directable tip (1605), comprising the steps of:

executing the following steps in at least one digital data processing unit (1601) and at least one computer readable storage medium (1608) that is included in or coupled with the at least one digital data processing unit (1601):

embodying, in the at least one computer readable storage medium, a configuration space data structure representing a physical task space that surrounds the directable tip (1605) of the non-holonomic physical tool (1604) in physical reality, the configuration space data structure including information representing the pose of the directable tip (1605) in the physical task space as 3 position values and 3 orientations and representing the pose at each reachable neighbor thereof as a change in the pose comprising changes in the 3 positional values and the 3 orientations of the directable tip (1605) required to transition to a reachable neighbor, and propagating cost waves (770), in the configuration space data structure, to fill a part of the configuration space data structure between the start and goal with cost values according to a space variant metric, the cost values representing physical aspects of the physical task space with respect to physical motion of the directable tip (1605) of the non-holonomic physical tool.

13. The method (700) of claim 12, wherein the step of propagating of waves (770) further comprises the step of being guided by a heuristic between.

14. The method of (700) claim 12, further comprising the steps of:

deriving (701) a sequence of directable tip pose representations within the configuration space data structure (1608), using the cost values, which representations represent physical poses defining a least cost path (1606) from a start pose to a goal pose in the physical task space; and providing the sequence (1606) in an electronic form usable by the non-holonomic physical tool (1604) to follow the path (1606).

15. The method (700) of claim 14, wherein the method further comprises the step of controlling the directable tip (1605) by at least one of an automatic control (1607) and an interventionalist (1602) such that the directable tip (1605) follows the least cost path (1606).

16. A method (700) for determining at least one physical motion specification (1606) for a non-holonomic physical tool (1604) having a directable tip (1605), comprising the steps of:

executing the following steps in at least one digital data processing unit (1601) and using at least one computer readable storage medium (1608) that is included in or coupled with the at least one digital data processing unit (1601):

i. embodying, in the at least one computer readable storage medium (1608), a data structure representing a physical task space that surrounds the directable tip (1605) of the non-holonomic physical tool (1604) in physical reality, the data structure including data representing the directable tip (1605) and the physical task space environment, the data structure including a plurality of nodes which are data structures representing physical poses of the directable tip (1605) based on assumable angles of the directable tip (1605) in the physical task space; and ii. propagating cost waves (770) in the data structure by performing the steps of:

a) determining a cost to goal for each neighbor of a home node in the data structure (730); and b) when an improved cost to goal value is determined for a neighbor, performing the steps of:

i. assigning (1603) the improved determined cost to goal to the neighbor of the home node, which cost to goal represents physical aspects of the physical task space and the physical motion of the directable tip (1605) and cost_to_goal; and ii updating neighbors (770) with the improved determined cost to goal and a pointer to the home node as a best parent in the storage data structure (1608).

17. The method (700) of claim 16, further comprising the step of controlling the non-holonomic physical tool (1604) to follow the path (1606).

18. The method (700) of claim 16, further comprising the steps of:

deriving a sequence (1606) of directable tip pose representations within the data structure, using the cost values, which representations represent physical poses defining a least cost path (1606) from a start pose to a goal pose in the physical task space; and providing the sequence (1606) in an electronic form usable by a controller (1602, 1607) of the directable tip (1001) to follow the path (1606).

19. The method (700) of claim 16, further comprising the steps of:

first transforming the physical goal pose into information of at least one goal state in the data structure;

second transforming a physical start pose into information of a start state;

assigning costs to states in the data structure so that each respective reachable state is assigned a cost value which represents the cost of an optimal path from the state to the goal state; and following the start state to the goal state to obtain a sequence (1606) of object pose representations within the data structure, which representations represent physical poses defining a least cost path (1606) from the start pose to the goal pose in the physical task space.

20. The method (700) of claim 19, further comprising the steps of:

determining, after the second transforming step, whether the path exists using a pre-determined algorithm; and stopping the method after the determining step, when it is determined that no path exists.

21. The method (700) of claim 19, wherein the assigning step further comprises evaluating cost according to a space variant metric function.

22. The method (700) of claim 19, further comprising the step of controlling the non-holonomic physical tool (1604) to follow the path (1606).

23. The method (700) of claim 19, wherein the assigning step further comprises the step of measuring (1603) cost values of transitions between neighboring states with a metric.

24. The method (700) of claim 23, wherein the assigning step further comprises the step of minimizing a function of stress and strain on the directable tip (1605) in the task space by increasing cost according to a predetermined cost function of stress and strain on the directable tip (1605).

25. The method (700) of claim 19, wherein the assigning step further comprises the step of evaluating cost according to a space variant metric function wherein constrained points in the physical task space are expressed as requiring higher cost transitions in the data structure.

26. The method (700) of claim 19, further comprising the step of third transforming at least one physical obstacle in the physical task space into at least one obstacle node in the data structure; and
   wherein, the assigning step further comprises the step of assigning cost such that each optimal path avoids the at least one obstacle node, such that the following step results in a path which avoids the obstacle.

27. The method (700) of claim 26, wherein the third transforming step further comprises assigning a substantially infinite value of cost to the at least one obstacle node, whereby the at least one obstacle node becomes part of a space variant metric function which measures cost.

* * * * *